US012678543B2

(12) United States Patent
Yang et al.

(10) Patent No.: US 12,678,543 B2
(45) Date of Patent: Jul. 14, 2026

(54) BIOACTIVE IMPLANT FOR RECONSTRUCTION OF BONE DEFECT, DEFORMITY, AND NONUNION

(71) Applicant: The Board of Trustees of the Leland Stanford Junior University, Stanford, CA (US)

(72) Inventors: Yunzhi Yang, Stanford, CA (US); Sien Lin, Sha Tin (CN); Seyedsina Moeinzadeh, Mountain View, CA (US); Elaine Lui, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 18/717,287

(22) PCT Filed: Dec. 9, 2022

(86) PCT No.: PCT/US2022/052412
§ 371 (c)(1),
(2) Date: Jun. 6, 2024

(87) PCT Pub. No.: WO2023/114104
PCT Pub. Date: Jun. 22, 2023

(65) Prior Publication Data
US 2024/0416014 A1 Dec. 19, 2024

Related U.S. Application Data

(60) Provisional application No. 63/304,207, filed on Jan. 28, 2022, provisional application No. 63/304,216, (Continued)

(51) Int. Cl.
*A61L 31/16* (2006.01)
*A61B 17/72* (2006.01)
(Continued)

(52) U.S. Cl.
CPC .............. *A61L 31/16* (2013.01); *A61B 17/72* (2013.01); *A61L 27/34* (2013.01); *A61L 27/52* (2013.01);
(Continued)

(58) Field of Classification Search
CPC ...................................................... A61B 17/72
See application file for complete search history.

(56) References Cited

U.S. PATENT DOCUMENTS 6,993,406 B1 1/2006 Cesarano, III
2005/0220837 A1 10/2005 Disegi
(Continued)

OTHER PUBLICATIONS

Fan et al. Engineered 3D Polymer and Hydrogel Microenvironments for Cell Culture Applications. Bioengineering 2019, 6, 113; doi:10.3390/bioengineering6040113.

*Primary Examiner* — Andrew Yang
(74) *Attorney, Agent, or Firm* — LUMEN PATENT FIRM

(57) ABSTRACT

A bioactive orthopedic implant is provided defined as a rod with a surface and a treated surface area for increased surface area, a freeze-dried hydrophilic hydrogel network physically cross-linked via charged polymers and salt-ions onto the treated surface area, biologies trapped and thereby hosted within the hydrogel network, and covalently reactive macromonomers chemically cross-linked within the hydrogel network to strengthen the hydrogel network itself and to the rod. The surface area of the bioactive orthopedic implant can be coated with covalently linkable molecules which are chemical cross-linked with the covalently reactive macromonomers to increase adhesion of the chemically and physically cross-linked hydrophilic hydrogel network to the rod. The rod can be an interconnected porous rod and where the biologies is hosted with pores of the interconnected porous rod. The bioactive orthopedic implant can be sized
(Continued)

for implantation in between two bone segments, a bone tunnel, or a fracture.

17 Claims, 21 Drawing Sheets

Related U.S. Application Data filed on Jan. 28, 2022, provisional application No. 63/289,431, filed on Dec. 14, 2021, provisional application No. 63/289,447, filed on Dec. 14, 2021.

(51) Int. Cl.

| | |
|---|---|
| *A61L 27/34* | (2006.01) |
| *A61L 27/52* | (2006.01) |
| *A61L 27/54* | (2006.01) |
| *A61L 27/56* | (2006.01) |
| *A61L 31/04* | (2006.01) |
| *A61L 31/06* | (2006.01) |
| *A61L 31/14* | (2006.01) |
| *A61B 17/56* | (2006.01) |

(52) U.S. Cl.
CPC .............. *A61L 27/54* (2013.01); *A61L 27/56* (2013.01); *A61L 31/042* (2013.01); *A61L 31/047* (2013.01); *A61L 31/06* (2013.01); *A61L 31/145* (2013.01); *A61L 31/146* (2013.01); *A61B 2017/561* (2013.01); *A61L 2300/252* (2013.01); *A61L 2300/414* (2013.01); *A61L 2300/606* (2013.01); *A61L 2400/18* (2013.01); *A61L 2420/02* (2013.01); *A61L 2420/08* (2013.01); *A61L 2430/02* (2013.01)

(56) References Cited

U.S. PATENT DOCUMENTS

| | | |
|---|---|---|
| 2008/0241214 A1 | 10/2008 | Myung |
| 2018/0133368 A1 | 5/2018 | Misra |
| 2018/0177597 A1 | 6/2018 | Chung |

IM Implant locking site

Regenerate site

Bone segment

IM implant

Bone defect

Docking site

Bone transport

Tunnel for implantation

IM implant locking site

Osteotomy

IM implant

Bone lengthening

Tunnel for implantation

IM implant locking site

Non-union

IM implant

Nonunion

IM implant locking site

Bone defect

IM implant

Bone defect

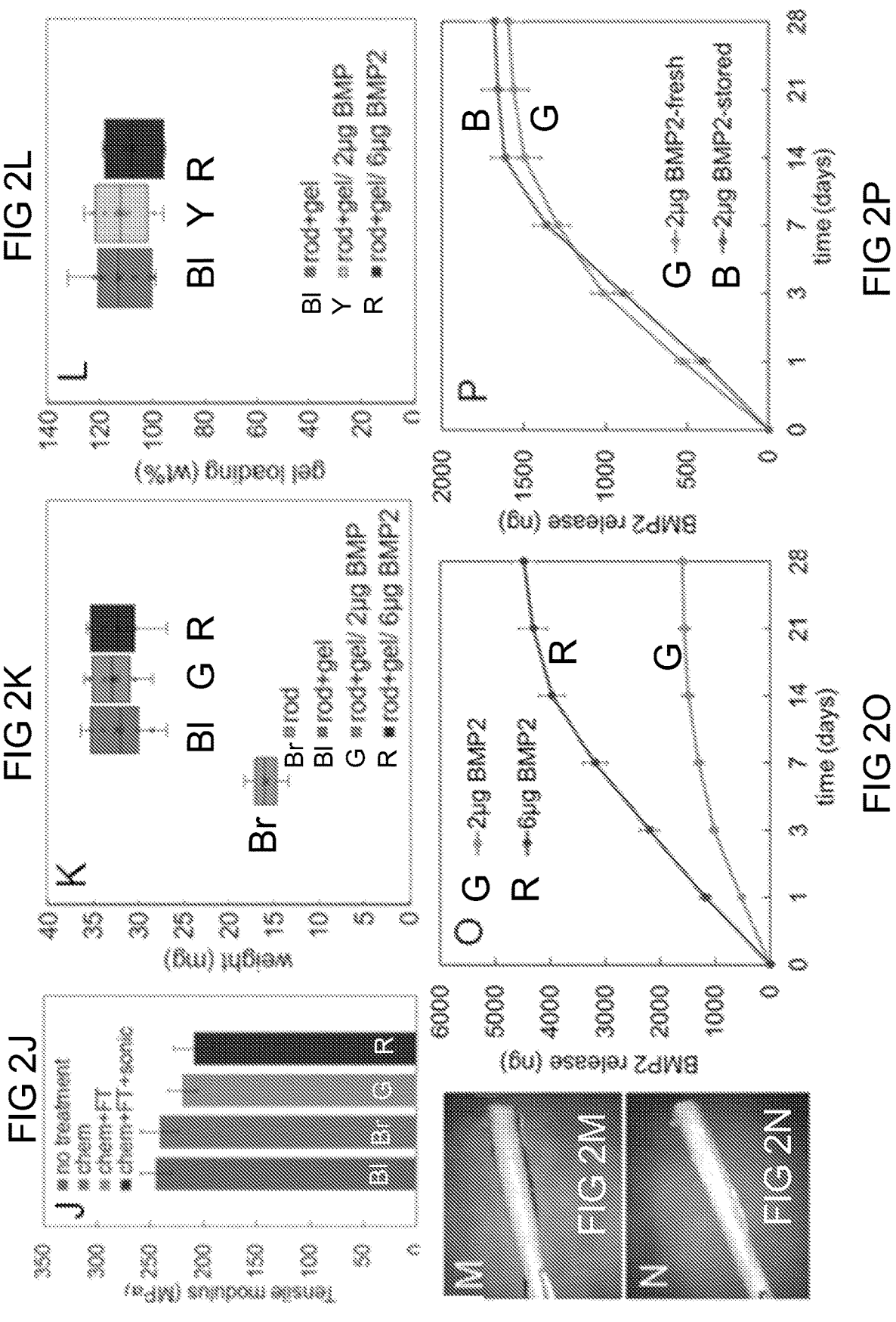

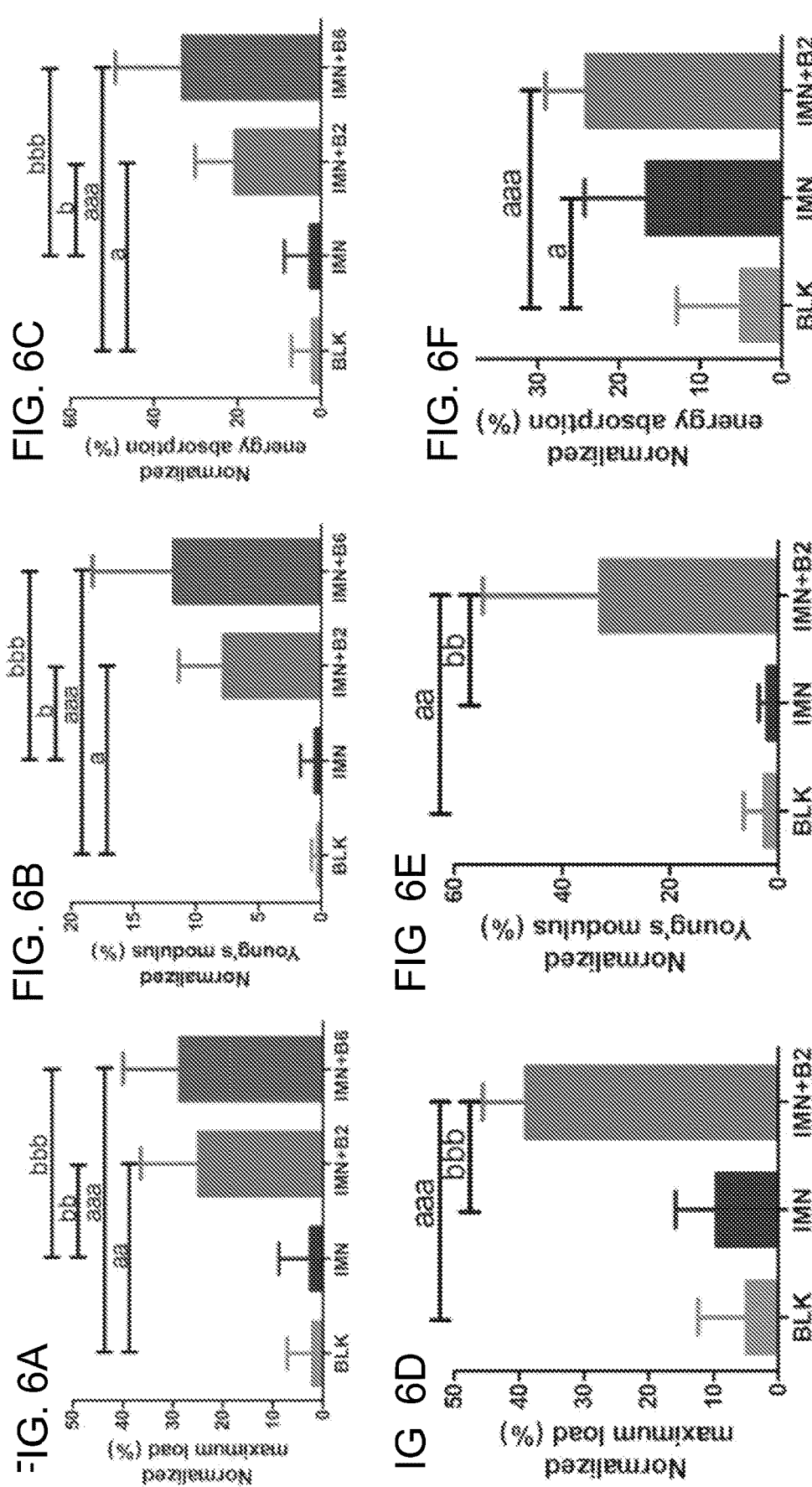

HyTEC with a protective layer for delayed release mHyTEC (1L)                    mHyTEC (3L)

HyTEC with a protective layer for delayed response

IMN+B6

IMN+B2

IMN

BLK

Docking Site

Regeneration Site

1510

1520

1510

1510

1520

1510

1510

1510

1510

1520

1510

1520

1510

1510

1510    1520

1530

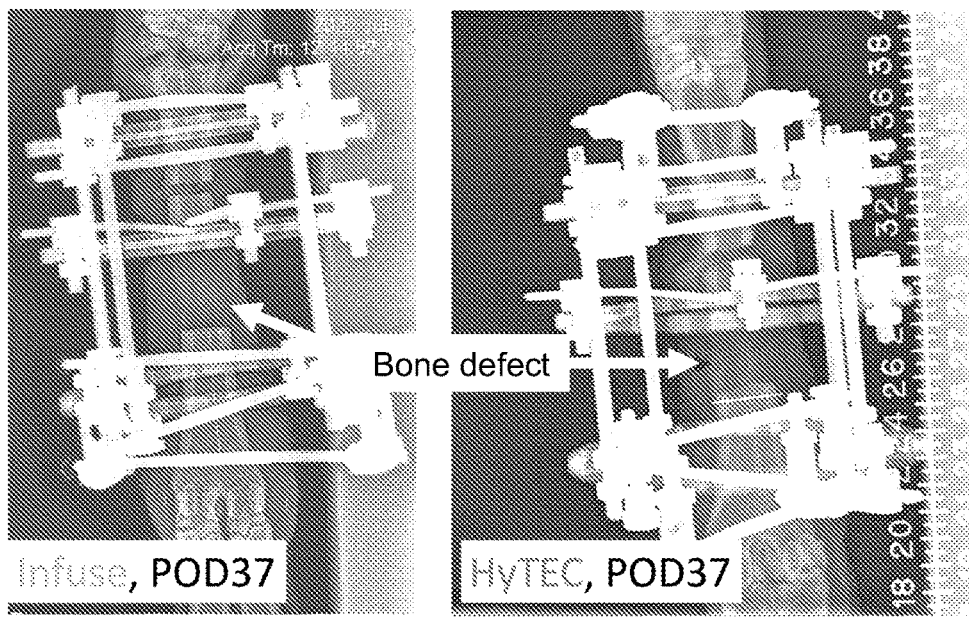
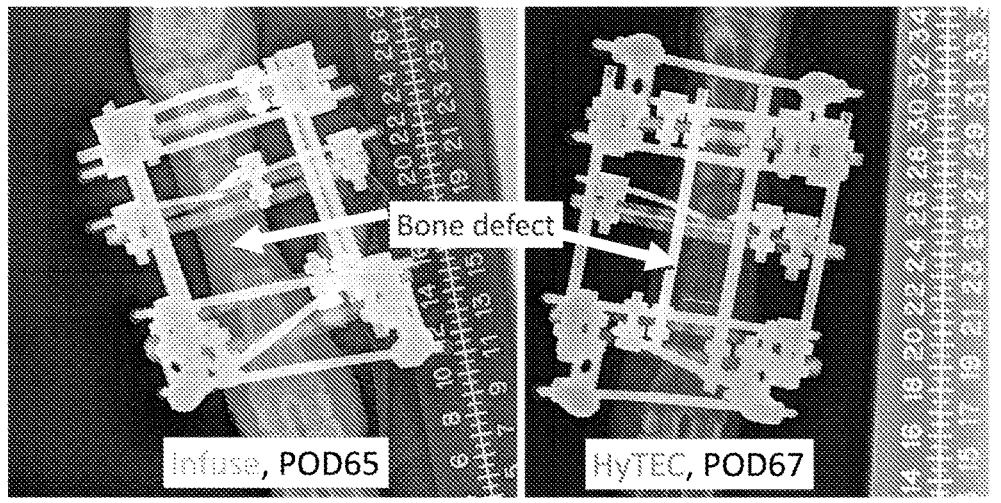
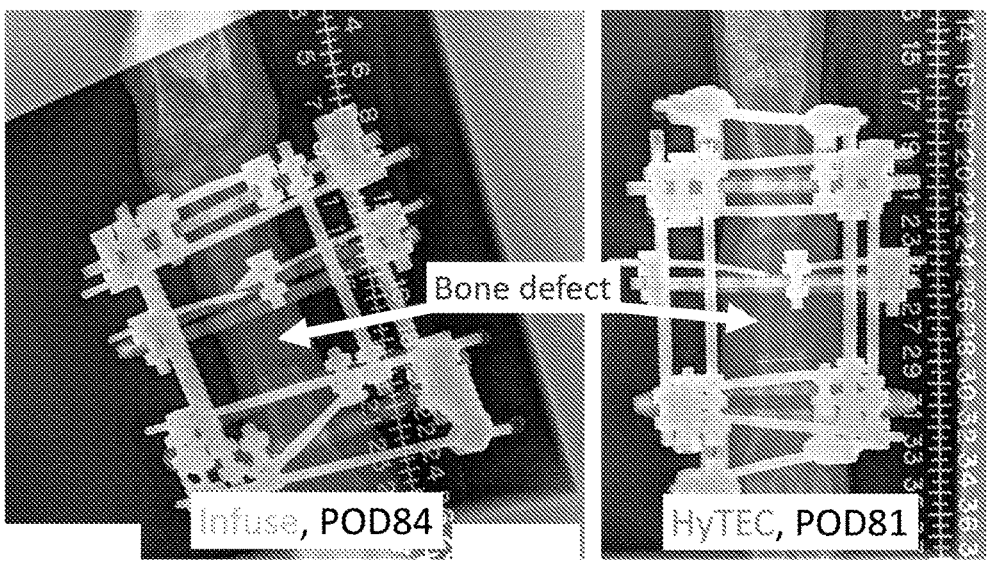
FIG. 16

BIOACTIVE IMPLANT FOR RECONSTRUCTION OF BONE DEFECT, DEFORMITY, AND NONUNION

FIELD OF THE INVENTION

This invention relates to bioactive implant for reconstruction of bone defect, deformity, and nonunion.

BACKGROUND OF THE INVENTION

Segmental bone defects resulted from high-energy trauma, debridement procedures, or tumor resection remain great challenges in the field of orthopedics. With the combined functions of mechanical support and osteo-regeneration, autogenous or allogenic bone grafting was regarded as the traditional procedures to bridge segmental bone defects. However, these procedures usually result in a decline in patient mobility and require multiple operations that are only effective in limited extent of bone defect reconstruction.

Modern limb salvage techniques of fracture stabilization or reconstruction have been applied to manage large bone defects for decades. In particular, the Ilizarov technique, also called distraction osteogenesis (DO), represents a relatively mature limb salvage procedure in the treatment of large bone defects. This procedure starts with an osteotomy, followed by lengthening over an external fixator or internal flexible fixator. According to the different types of treatment, Ilizarov technique includes three categories: acute shortening and lengthening (monofocal approach), single-level bone transport (bifocal approach) or double-level bone transport (trifocal approach). The monofocal approach has been recommended in management of small size bone defect (usually <2 cm) by closing bone defects directly before lengthening. However, when the defect size greater than 3 cm, acute shortening may affect the soft tissue and compromise the vasculature, leading to limb ischemia. The bifocal approach utilizes an osteotomy away from the defect site. The intercalary segment is then transported away from the corticotomy site and compressed at the defect site to maintain optimal bone length. A trifocal approach uses two lengthening osteotomies in addition to compression of the defect. The bifocal or trifocal approach has shown some advantages in treatment of larger bone defect without limb discrepancy and soft tissue contraction. However, there are still several disadvantages to using bone transport methods, such as pin track infection, docking site nonunion and insufficient bone consolidation. Among these, docking site nonunion was found in almost all of the patients subjected to bone transport as inactive bone contact and soft tissue intrusion at the docking site has the tendency to form a pseudarthrosis. Secondary debridement and bone grafting surgery are always essential to achieve a final bone bridging at the docking site. Recently, an increasing number of reports have addressed bone transport over a metallic intramedullary (IM) nail as a method of reducing the period of external fixation. However, there is no reliable evidence to suggest that the metallic IM nail can achieve early consolidation or decline in docking site nonunion, and an additional surgery may be needed to remove the metallic IM nail.

Bone morphogenetic proteins (BMPs) are among the most potent osteoinductive factors that play a crucial role in bone repair or regeneration. A DO animal model showed that BMP-2, -4, and -7 were highly expressed at the regenerate site during distraction phase, and then gradually diminished during the consolidation phase. Local injection of recombinant human (rh) BMP-2 or BMP7 has been shown to accelerate bone formation in a number of DO models. The inventors postulated the question whether one would be able to accelerate bone healing and reduce nonunion in bone transport by introducing a biodegradable IM nail to sustain delivery of BMP in a single surgery procedure, without secondary operations, grafting, or severe complications. The present invention addresses at least some of these questions.

SUMMARY OF THE INVENTION

In one embodiment, a method is provided of reconstructing of a bone defect, deformity or nonunion. A bioactive implant is provided, which has a scaffold, a freeze-dried hydrogel network layer physically and chemically crosslinked and chemically bound to the scaffold, and biologics distributed and hosted within the freeze-dried hydrogel network layer. In one embodiment, the bioactive implant further has a coating.

The bioactive implant, sized for implantation in between two bone segments, a bone tunnel, or a fracture, is implanted in between two bone segments, a bone tunnel, or fractured bones. In the case where the bioactive implant is used as an intramedullary bioactive implant it is then sized for intramedullary implantation in between two bone segments. In the case where the bioactive implant is used for a surgically created bone tunnel for the treatment of trauma and disorders of the foot and ankle, shoulder, hip or joints, it is then sized or slightly bigger for press fit for the bone tunnel that is surgically created in the anatomical locations that are intended to be treated.

In another embodiment, the scaffold is an interconnected porous scaffold. The freeze-dried hydrogel network layer is physically and chemically crosslinked and chemically bound to the interconnected porous scaffold, and the biologics is further also distributed and hosted in the freeze-dried hydrogel on the surfaces and in the pores of the interconnected porous scaffold.

In yet another embodiment, a bioactive implant for an orthopedic application is provided. The bioactive implant has a scaffold, a freeze-dried hydrogel network layer physical and chemically crosslinked and chemically crosslinked to the scaffold, and biologics distributed and hosted within the freeze-dried hydrogel network layer. The bioactive implant is sized for implantation in between two bone segments or fractured bone. In the case where the bioactive implant is used as an intramedullary bioactive implant it is sized for intramedullary implantation in between two bone segments. In one embodiment, the bioactive implant has been coated.

In yet another embodiment, the scaffold is an interconnected porous scaffold, the freeze-dried hydrogel network layer is physically and chemically bound to the interconnected porous scaffold and the biologics is further distributed and hosted on the surfaces and in the pores of the interconnected porous scaffold.

In still another embodiment, the present invention is a bioactive (intramedullary (IM)) implant device-based therapy for the improved treatment of long bone defects, correction of bone deformities, or healing of bone nonunion. The bioactive implant devices have core scaffolds and bioactive hydrogel coatings. The core scaffolds can be polymer, ceramic, metal, or their composites. The core scaffolds can be porous or non-porous and degradable or non-degradable. The hydrogels can be interpenetrating networks of a physically crosslinked gel and a covalently crosslinked gel. A hydrogel example can be gelatin methacryloyl-alginate-based (GelMA-alginate) gel. Small molecular weight crosslinkers can be added to the hydrogel to increase the crosslink density. The bioactive materials include growth factors and drugs. Growth factors can be BMP-2, PDGF, IGF-1, FGF2, and others and be loaded into the hydrogel and exhibit a tunable or sustained-release pattern. The device can used as an adjunctive therapy to distraction osteogenesis and other orthopedic trauma and disorders for (FIGS. 1A-D):

(1) bone transport over an IM implant;

(2) bone lengthening over an IM implant;

(3) bone healing over an IM implant or an implant that is sized for the bonne tunnel for the treatment of nonunion and disorders; or (4) bone defect healing over an IM implant.

It is noted that the bioactive implant device is not limited to intramedullary applications as it could also be used in a regular bone graft place between bones or bone defects, and not necessarily in the intramedullary space. The scaffold (or IM nail) could be a solid rod or a porous scaffold, in particular a metal rod could be load bearing.

The device can effectively accelerate bone consolidation in bone lengthening and prevent docking site nonunion when patients are subjected to bone transport surgery. The device can also effectively promote bony fusion in the treatment of nonunion. FIGS. 1A-D show the schematic design of this implant device for bone healing under three different conditions.

In another embodiment the invention can be characterized as an implant device with a scaffold and coating materials. The core scaffold materials can be composites, including polymers, ceramics, metal, composites, etc., such as poly-caprolactone-tricalcium phosphate (PCL-TCP) and poly (lactic-co-glycolic acid-TCP) PLGA/TCP. PCL-TCP filaments in a weight ratio of 80:20 (w/w) can be printed into 3D porous scaffold with pore size in the range of 100 $\mu$m to mm. The core material can be also metallic materials, such as titanium alloys, cobalt-chromium alloys, magnesium alloys, zinc alloys, etc. The core scaffolds can be porous or non-porous. The hydrogel coating layer could cover the entirety or part of the core scaffold.

Regarding the implantation, there are four different methods, depending on the three applications (FIGS. 1A-D). (1) For the treatment of (large) bone defect, the device can be inserted into the distal and proximal bone segments through the defect gap or in a minimally invasive way during the bone transport operation. The hydrogel coating layer should cover the length from regenerate site to docking site. The two ends of device can be secured by the distal and proximal fixative pins. Of note, the pin for transporting the middle bone segment should avoid any contact with the IM device. (2) For bone lengthening, the device can be inserted antero-gradely or retrogradely into the long bone in a minimally invasive way. The hydrogel coating layer should cover the length of the regenerate site. The device can only be secured by distal or proximal pins. (3) For the treatment of non-union, the device can be inserted anterogradely or retro-gradely into the long bone in a minimally invasive way during surgical debridement. The hydrogel coating layer should cover the length of non-union gap. The device can be secured by distal and proximal pins. (4) For the treatment of bone defect, the device can be inserted into the distal and proximal bone segments through the defect gap. The hydro-gel coating layer should cover the length of defect gap. The device can be secured by distal and proximal pins or internal or external fixators such as plates or IM nail.

An example of biologically-loaded hydrogel coatings is presented below. The hydrogel coating contains gelatin methacrylate (GelMA, 15%), alginate (1.25%), poly(ethyl-ene glycol) dimethacrylate (PEGDMA, 2%), heparin meth-acrylate (HepMA, 1%), bone morphogenetic protein-2 (BMP-2, 200 $\mu$g/mL), and photoinitiator (0.3%) in deionized water. To synthesize GelMA macromonomer, gelatin was dissolved in deionized water (10% w/v) at 50° C. To synthesize methacrylated heparin (HepMA), 1 g heparin was dissolved in 100 mL MES buffer (100 mM). 5 mL MES buffer containing 45 mg EDC and 30 mg NHS was then added to the heparin solution to activate the carboxylic acid groups as described. After 1 hr reaction at room temperature, 25 mg APMA in 1 mL MES was added to the solution and allowed to react for 2 hr at room temperature. The HepMA solution was then dialyzed against deionized water using a dialysis tube (Spectrum Laboratories, Rancho Dominquez, CA) with 6-8 kDa molecular weight cutoff for 3 days at ambient temperature, lyophilized, and stored at −80° C.

An example of bioactive implant devices is presented below. For example, polycaprolactone-beta-tricalcium phos-phate (PCL-TCP) filaments with BMP-2-laden hydrogel was fabricated as shown in FIGS. 2A-P. PCL-TCP filaments in a weight ratio of 80:20 (w/w) with 0.9-mm in diameter were synthesized as described before, manually cut to make 15 mm filaments, and dipped into a 5N NaOH solution for 6 hours. The filaments were then washed three times with Deionized water and incubated in an MES buffer (100 mM) containing EDC (5 mg/mL) and NHS (5 mg/mL) for 30 min at room temperature in order to activate the carboxylic acid groups on the surface. Then, the filaments were washed three times with Deionized water and incubated in gelatin meth-acrylate (GelMA) 2% solution in MES buffer for 1 hour at 37° C. The filaments were then washed three times with Deionized water to remove the unreacted GelMA and incu-bated in EDC/NHS (5 mg/mL) in MES buffer solution for 15 minutes at room temperature. The GelMA coated filaments were then washed three times with Deionized water and dried under vacuum. Then, the GelMA coated filaments were dipped into a $CaSO_4$ suspension in Deionized water (100 mg/mL) at 60° C. and sonicated for 30 seconds. The filaments were then transferred into wells of a 24-well plate and dried under vacuum. The dried filaments were dipped into wells of a 96-well plate containing GelMA (15%), alginate (1.25%), PEGDMA (2%), HepMA (1%), protein (BMP-2,200 $\mu$g/mL), and photoinitiator (0.3%) in Deionized water at 37° C. for 2 minutes. The hydrogel-loaded filaments were removed from the solution and left in dry wells of another 96-well plate for 5 minutes. The hydrogel-loaded filaments were then irradiated with visible light for 15 minutes to covalently crosslink GelMA, PEGDMA, and and HepMA. The crosslinked hydrogel-loaded filaments were stored at −80° C. and freeze-dried.

An example of in vivo validation of the bioactive implant devices to promote bone regeneration using a rat bone transport model is shown in FIGS. 3A-H, 4A-C, 5A-C, 6A-F, 7. FIGS. 3A-H show ex vivo and in vivo demonstra-tion of bone transport by a customized metallic distraction fixator. FIGS. 4A-C show gross observation and union rate of the femoral samples harvested on postoperative day 34 (POD34) or postoperative day 55 (POD55). FIGS. 5A-C show 3D reconstructed images and quantitative bone mass data of the affected femurs on POD34 or POD55 measured by micro-CT analysis. FIG. 6 shows mechanical properties measured by 3-point bending tests of the affected femurs normalized by their contralateral compartments on POD34 or POD55. FIG. 7 shows representative histological results of the affected femurs on POD34 or POD55.

Mechanical properties were also significantly increased in the intramedullary nail loaded with 6 g BMP2 (IMN+B6) group by 26.6% (P<0.001), 11.6% (P<0.001), or 31% (P<0.001) in normalized maximum load, Young's modulus, and energy absorption when compared with those in the blank control (BLK) group on POD34 or 26.1% (P<0.001), 11.3% (P<0.001), or 30.5% (P<0.001) when compared with those in the intramedullary nail (IMN) group on POD34 (FIGS. 6A-F). However, there is no significant difference in the mechanical properties in the (EVIN+B6) group when compared with those in the intramedullary nail loaded with 2 μg BMP2 (IMN+B2) group on POD34 (FIGS. 6A-F).

Histological data showed the longitudinal images of affected femurs, including the docking sites and regeneration sites (FIG. 7). From the results, we showed the evidence of soft tissue interposition at the docking sites of BLK group and the IMN group on POD34 and POD55 (FIG. 7). However, bony fusion was found at the docking sites in the (IMN+B2) and (IMN+B6) groups on POD34 and POD55, with no soft tissue interposition (FIG. 7). Newly formed bone could be found at the regeneration site in all the groups on POD34 and POD55 (FIG. 7). Pin track infections could be found in some of the samples in BLK and IMN groups on POD34 and POD35 (FIG. 7). Cortical and trabecular bone could be clearly identified at regenerate sites as well as docking sites in the (IMN+B2) group on POD55, indicating bone remodeling was also enhanced in the animals (FIG. 7). A much higher quantity of newly formed bone could be also found at the implant site in the (IMN+B2) and (IMN+B6) group (FIG. 7).

Embodiments of the invention can be applied as intramedullary implant devices for delivery of growth factors in bone healing. Examples are as follows:

metallic, polymeric, or composite implant to deliver growth factors for the treatment of long bone defect adjunctive to bone transport technique;

metallic, polymeric, or composite implant to deliver growth factors for the correction of bone deformity adjunctive to bone lengthening technique;

metallic, polymeric, or composite implant to deliver growth factors for the treatment or prevention of nonunion; or antibiotic-laden metallic, polymeric, or composite implant for bone transport or bone lengthening.

Embodiments of the invention are advantageous in areas where segmental bone defects result from high-energy trauma, debridement procedures, or tumor resection as they remain great challenges in the field of orthopedics. With the combined functions of mechanical support and osteo-regeneration, autologous or allogenic bone grafting was regarded as the traditional procedures to bridge segmental bone defects. However, these procedures usually result in a decline in patient mobility and require multiple operations that are only effective to the limited extent of bone defect reconstruction. Modern limb salvage techniques of fracture stabilization or reconstruction have been applied to manage large bone defects for decades. In particular, the Ilizarov technique, also called distraction osteogenesis (DO), represents a relatively mature limb salvage procedure in the treatment of large bone defects. This procedure starts with an osteotomy, followed by lengthening over an external fixator or internal flexible fixator. According to the different types of treatment, Ilizarov technique includes three categories: acute shortening and lengthening (monofocal approach), single-level bone transport (bifocal approach), or double-level bone transport (trifocal approach). The monofocal approach has been recommended in management of small size bone defect (usually <2 cm) by closing bone defects directly before lengthening.

However, when the defect size is greater than 3 cm, acute shortening may affect the soft tissue and compromise the vasculature, leading to limb ischemia. The bifocal approach utilizes an osteotomy away from the defect site. The intercalary segment is then transported away from the corticotomy site and compressed at the defect site to maintain optimal bone length. A trifocal approach uses two lengthening osteotomies in addition to compression of the defect. The bifocal or trifocal approach has shown some advantages in treatment of larger bone defect without limb discrepancy and soft tissue contraction. However, there are still several disadvantages to using bone transport methods, such as pin track infection, docking site nonunion, and insufficient bone consolidation. Among these, docking site nonunion is found in almost all of the patients subjected to bone transport, as inactive bone contact and soft tissue intrusion at the docking site has the tendency to form pseudoarthroses. Secondary debridement and bone grafting surgery are essential to achieve a final bone bridging at the docking site. Recently, an increasing number of reports have addressed bone transport over a metallic intramedullary (IM) nail as a method of reducing the period of external fixation.

However, there is no reliable evidence to suggest that the metallic nail can achieve early consolidation or decline in docking site nonunion, and an additional surgery is needed to remove the metallic nail as a final step.

The bioactive implant device according to this invention is developed with consideration of available regulatory pathways, manufacturing processes, distribution, and clinical applicability to address significant clinical challenges such as docking site non-union and slow bone consolidation. First, the bioactive implant devices are based on FDA cleared materials and growth factors, which is applicable for a fast 510(K) regulatory pathway. Second, the bioactive implant devices are compatible with the current surgical treatment and can be easily adapted by orthopedic surgeons, the end users. Third, the bioactive implant device can be implanted in a single surgery that is needed for defect or facture fixation for the treatment of long bone defects, bone deformities, or nonunion. The intramedullary device can be inserted to the proximal and distal ends of bone segments or inserted through a bone tunnel in a minimally invasive way. The devices can be anchored in site by the fixative pins. Fourth, a secondary surgery is not needed for removing the tissue at the nonunion site and implant allograft in bone transport DO. No allograft is needed during surgery for nonunion. The devices can be biodegradable if using biodegradable biomaterials. The device could also provide mechanical support if using metallic materials. Fifth, the storage and transportation conditions of this bioactive device are friendly, making it convenient for manufacturers, distributors, and surgeons, the end users.

The scaffold for implant device can be polymeric, metallic or composite materials. After different surface treatments, the device can be coated with hydrogel loading with different growth factors, with different doses, depending on the applications.

In one embodiment, to slow down the release of therapeutics, the bioactive implants (e.g. HyTEC constructs) could be coated with a resorbable polyester (e.g. PCL, PLA, or PLGA) or other resorbable polymers (e.g. polyurethanes). HyTEC stands for hybrid tissue engineered construct, which is a bioactive implant. A schematic representation of the method that is used to coat the HyTEC constructs is shown in FIG. 8. For instance, protein-laden HyTEC is freezed at −80° C. overnight followed by 10 minutes freezing at −20° C., and dipped in a solution of PCL in acetone or chloroform (2%-20%) to deposit a layer of PCL on HyTEC and make a modified HyTEC (mHyTEC). Then the PCL-coated HyTEC is air-dried at 0-4° C. The concentration of PCL solution and the number of deposited PCL layers could be changed to tune the physical characteristics of mHyTEC constructs and release kinetics of proteins. Representative images of mHyTEC with 1 layer of PCL coating (mHyTEC (1 L)) and 3 layers of PCL coating (mHyTEC (3 L)) are shown in FIG. 9. While 92% of the encapsulated BSA was released from BSA-laden HyTEC without coating after 14 days, the rate of BSA release was reduced to 92% after 70 days or 80% in 91 days, with addition of 1 layer or 3 layers of protective PCL coating using a PCL/acetone (10% wt/v) solution (FIG. 10). Also, the amount of released bone morphogenic protein 2 (BMP2) protein from BMP2-laden HyTEC constructs after 28 days in PBS decreased was 84% to 62% or 24% with deposition of 1 layer or 3 layers of PCL coating (FIG. 11).

In another characterization, the invention could be described as follows. Distraction osteogenesis represents one of the most successful surgical approaches for the treatment of large segmental bone defects. However, the noticeable complications include prolonged consolidation and docking site nonunion, especially when involving bone transport procedures. The latter always requires secondary operations of bone grafting to achieve bone bridging. To this end, the inventors developed an osteoinductive biodegradable intramedullary (IM) nail by eluting bone morphogenetic protein-2 (BMP-2) from a biodegradable implant as an adjunctive therapy to address the clinical challenges of the bone transport technique above. For proof of concept, the inventors developed an IM nail and tested it in a rat long bone transport model. Firstly, the IM nail was fabricated with polycaprolactone-tricalcium phosphate (PCL-TCP) filament coated with gelatin methacryloyl-alginate (GelMA-alginate) hydrogel loading with BMP-2 (2 μg or 6 μg). The release profile of the BMP-2 in the TN nail was measured after lyophilization and sterilization. Then, the efficacy of the IM nail was evaluated in a rat femur bone transport model. The healing process was monitored by X-ray weekly. After 34 or 55 days of operation, the specimens were harvested for gross observation of pin track infection and bridging of segments, and assessments including mechanical properties, microstructure and morphology of the new bone formation at docking site Results showed that BMP-2 could sustain-release from the IM nail over 21 days. The femur transport model was successfully established with pin track infection and insufficient consolidation at both the docking site and regenerate site. The bone mass and 3-point bending mechanical strength of the BMP-2-incorported IM nail group were significantly greater than those of the surgical control group at POD34 and POD55. The BMP-2 incorporated IM nails also showed diminished pin track infection and promoted bony union at the docking sites. Histological data also confirm the superior effect of BMP-2 incorporated IM nail, with higher mineral apposition rates in the BMP-2 incorporated IM nails groups. No significant difference in the bone healing effect could be found between the two BMP-2 doses. Overall, the experiments demonstrated that the biodegradable BMP-2-incorporated IM nail implant significantly accelerated consolidation in DO, reduced pin infection, and improved docking site union rate, leading to weight-bearing capability and early external fixator removal without any secondary operations. This adjunctive therapy technique holds great promise to rejuvenate and revolutionize bone transport technique in large bone defects management and limb salvage in the future.

The invention can also be characterized as a method of reconstructing of a bone defect, deformity or nonunion. A bioactive orthopedic implant would be present, which is defined as a rod with a surface and a treated surface area for increased surface area, a freeze-dried hydrophilic hydrogel network physically cross-linked via charged polymers and salt-ions onto the treated surface area, biologics trapped and thereby hosted within the physically cross-linked freeze-dried hydrophilic hydrogel network, and covalently reactive macromonomers chemically cross-linked within the physically cross-linked hydrophilic hydrogel network to strengthen the physically cross-linked hydrophilic hydrogel network itself and to the rod. The bioactive orthopedic implant can then be implanted in between two bone segments or a bone tunnel. The bioactive orthopedic implant can be sized for implantation in between two bone segments, a bone tunnel, or a fracture. The bioactive orthopedic implant can also be sized for intramedullary implantation in between the two bone segments or the fracture. The interconnected porous rod includes embodiments of a central or internal channel in the porous scaffold/rod. The coating of the bioactive orthopedic implant can be over the entire rod or partially. As such also different coatings can be used for segments of the rod. All which depend on the type of reconstruction that is desired as a skilled artisan would readily appreciate. In addition, the bioactive orthopedic implant could have one or more (additional) coating layers. In a further embodiment, the rod can be an interconnected porous rod and wherein the biologics is hosted with pores of the interconnected porous rod.

The invention can further be characterized as a bioactive orthopedic implant, which can be defined as a rod with a surface and a treated surface area for increased surface area, a freeze-dried hydrophilic hydrogel network physically cross-linked via charged polymers and salt-ions onto the treated surface area, biologics trapped and thereby hosted within the physically cross-linked freeze-dried hydrophilic hydrogel network, and covalently reactive macromonomers chemically cross-linked within the physically cross-linked hydrophilic hydrogel network to strengthen the physically cross-linked hydrophilic hydrogel network itself and to the rod. The surface area of the bioactive orthopedic implant can be coated with covalently linkable molecules which are chemical cross-linked with the covalently reactive macromonomers to increase adhesion of the chemically and physically cross-linked hydrophilic hydrogel network to the rod. The rod can be an interconnected porous rod and where the biologics is hosted with pores of the interconnected porous rod. The bioactive orthopedic implant can be sized for implantation in between two bone segments, a bone tunnel, or a fracture. The bioactive orthopedic implant can also be sized for intramedullary implantation in between the two bone segments or the fracture. The coating of the bioactive orthopedic implant can be over the entire rod or partially. As such also different coatings can be used for segments of the rod. All which depend on the type of reconstruction that is desired as a skilled artisan would readily appreciate. In addition, the bioactive orthopedic implant could have one or more (additional) coating layers.

BRIEF DESCRIPTION OF THE DRAWINGS

If needed, for further interpretation of the gray-scale in the drawings the reader is referred to the priority document(s) for each of the respective figures.

(FIG. 1A) Bone transport over an implant. Two ends of implant are anchored by two fixative pins. (FIG. 1B) Bone lengthening over an implant. The implant can be inserted through a bone tunnel. One end of implant is anchored by one fixative pin. (FIG. 1C) Non-union treated with an implant. Two ends of implant are anchored by fixative pins. (FIG. 1D) A defect treated with an implant. Two ends of implant are anchored by fixative pins.

FIGS. 2A-P show according to an exemplary embodiment of the invention fabrication and characterization of the intramedullary (IM) nail implant. (FIG. 2A) A schematic procedure for making osteoinductive biodegradable IM nail implant. (FIG. 2J) Effect of chemical treatment (NaOH treatment and GelMA coating) without freezing/thawing or sonication (chem, Bl), chemical treatment with freezing/thawing but without sonication (chem+ FT, G), or chemical treatment with freezing/thawing and sonication (chem+FT+sonic, R) on the tensile modulus of the PCL-TCP filaments. The control group was PCL-TCP filaments without any treatment (no treatment, B). FIGS. 2K-L) Changes in weight (FIG. 2K) or percentage of weight FIG. 2L) of the PCL-TCP filaments without hydrogel coating (rod, Br), filaments with hydrogel coating but without BMP-2 loading (rod+gel, Bl), filaments with hydrogel coating with 2 g BMP-2 loading (rod+gel/2 g BMP-2, G), and filaments with hydrogel coating with 6 g BMP-2 loading (rod+gel/6 g BMP-2, R). (FIGS. 2M-N) Gross view of wet (FIG. 2M) or freeze-dried (FIG. 2N) BMP-2-laden hydrogel loaded implant. (FIG. 2O) Amount of released BMP-2 from freeze-dried hydrogel loaded implant with 2 μg (G) or 6 μg (R) BMP-2 in 28 days. (FIG. 2P) Amount of released BMP-2 from stored (Bl) or fresh (G) freeze-dried hydrogel loaded implant with 2 μg BMP-2 in 28 days. There were 8 samples per group for data in FIG. 2K and FIGS. 2L, and 3 samples per group for data in FIG. 2J, FIG. 2O, and FIG. 2P. Data shown in FIG. 2J, FIG. 2O, and FIG. 2P correspond to means±SD. Data shown in FIG. 2K and FIG. 2L correspond to mean and 95% confidence interval.

(FIG. 3A) Schematic design of the monolateral distraction frame (longitudinal section or side view); (FIG. 3B) Final products of distraction frame and pins after manufacturing. (FIG. 3C) Top view of distraction frame and pins fixed to a rat femur after osteotomy, corticotomy, and IM nail implantation. (FIGS. 3D-F) Bone slice was transported over an IMN from the proximal to the distal segment of femur. (FIG. 3G) Macro view of the operation after osteotomy and corticotomy. (FIG. 3H) Macro view of the IM nail implantation.

(FIG. 4A) Gross view of the femoral samples. White arrows point to the docking sites. Two white dash lines indicate regenerate sites. (FIG. 4B) Union rate as determined by the gross observation and micro-CT analysis. (FIG. 4C) Pin track infection rate assessed on POD34 or POD55 before sacrifice (n=8). Pin track infection was determined by Checketts-Otterburn classification. Only minor pin track infections were found in some of the animals before sacrificed, which included 1 to 2 pins loosening in one animal.

(FIG. 5A) Representative 3D images (longitudinal half-cut) of the affected femurs. Two regions of interest (ROIs) were highlighted by green dash rectangles or yellow dash rectangles, which representing the docking sites or regenerate sites. (FIG. 5B) Quantitative data of bone mass (bone volume/tissue volume, BV/TV) at docking site or regenerate sites on POD34. (FIG. 5C) Quantitative data of bone mass (BV/TV) at docking site or regenerate sites on POD55. Data are shown as mean value of normalized BV/TV and SD (n=8 per time point). $^aP<0.05$, $^{aa}P<0.01$, $^{aaa}P<0.001$, vs. BLK group; $^bP<0.05$, $^{bb}P<0.01$, $^{bbb}P<0.001$, vs. IMN group.

FIGS. 6A-F show according to an exemplary embodiment of the invention mechanical properties measured by 3-point bending tests of the affected femurs normalized by their contralateral compartments on POD34 or POD55. The animal groups included blank control group (BLK), IM nail only group (IMN), the 2 μg BMP-2-incorporated IM nail group (IMN+B2) and 6 μg BMP-2-incorporated IM nail group (IMN+B6). Mechanical parameters including normalized maximum load, Young's modulus, and energy absorption. (FIG. 6A-C) Results of mechanical properties on POD34. (FIG. 6D-F) Results of mechanical properties on POD55. Data are shown as mean and SD (n=8 per time point). $^aP<0.05$, $^{aa}P<0.01$, $^{aaa}P<0.001$, vs. BLK group; bP<0.05, $^{bb}P<0.01$, $^{bbb}P<0.001$, vs. EVIN group.

L), and with 3 layer of PCL coating made using a PCL/acetone (10% wt/v) solution (PCL/acetone-3 L).

Figure 11:
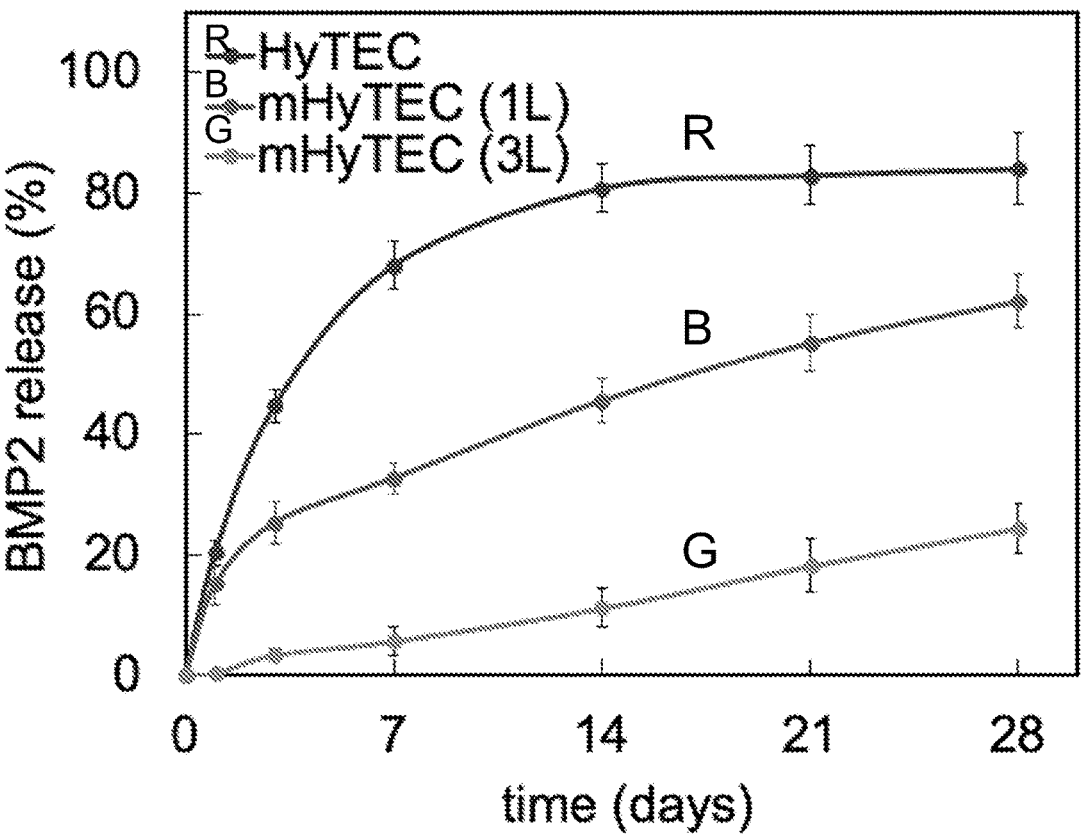

FIG. 11 shows according to an exemplary embodiment of the invention release kinetics of rhBMP2 from HyTEC constructs without PCL protective coating (HyTEC), with 1 layer of PCL coating made using a PCL/acetone (10% wt/v) solution (mHyTEC (1 L)), and with 3 layers of PCL coating made using a PCL/acetone (10% wt/v) solution (mHyTEC (3 L)).

Figure 12:
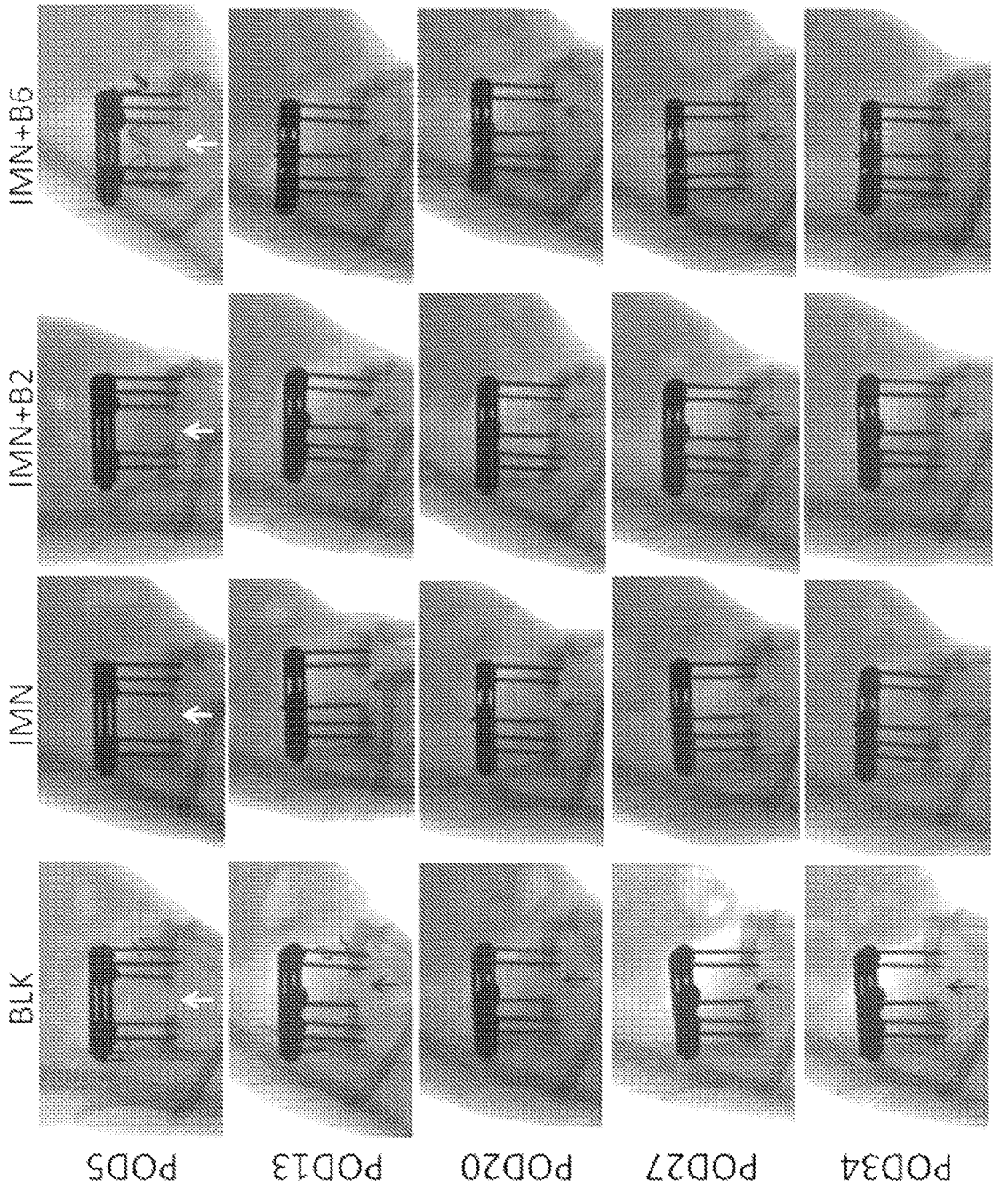

FIG. 12 shows according to an exemplary embodiment of the invention in vivo dynamic X-ray images of the affected femurs from POD5 to POD34. The animal groups included blank control group (BLK), IM nail only group (IMN), the 2 Mg BMP-2-incorporated IM nail group (IMN+B2) and 6 g BMP-2-incorporated IM nail group (IMN+B6). White arrows point to the bone defect sites before bone transport on PODS. Red arrows point to the bone defect sites after bone transport on POD13 to POD34 (3 weeks of consolidation).

Figure 13A:
Figure 13B:
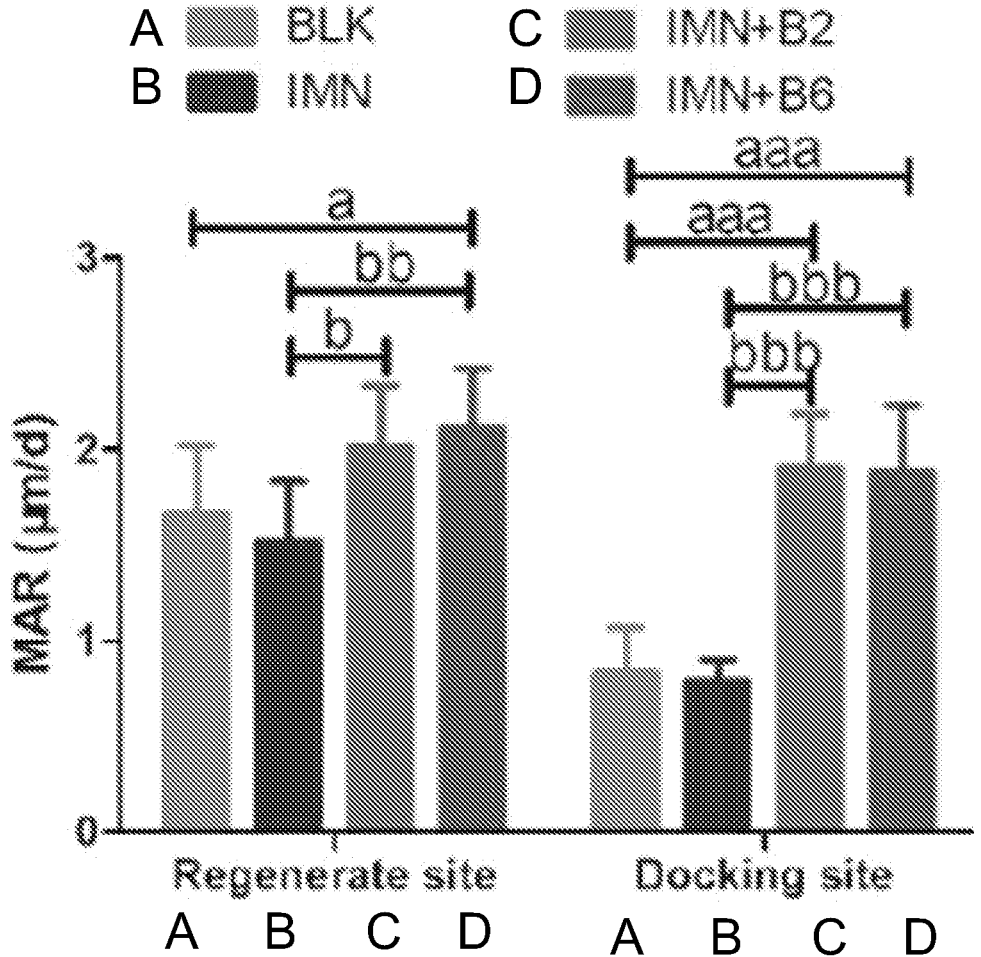

FIGS. 13A-B show according to an exemplary embodiment of the invention histomorphometry results of the affected femurs on POD34. The animal groups included blank control group (BLK), IM nail only group (IMIN), 2 ug BMP-2-incorporated IM nail group (IMN+B2) and 6 Mg BMP-2-incorporated IM nail group (IMN+B6). The white arrows indicate the distance between the green and red fluorescent dyes, representing mineral apposition in 10 days before sacrifice. Data are shown as mean and SD (n=3). $^{a}P<0.05$, $^{aa}P<0.01$, $^{aa}P<0.001$, vs. BLK group; bP<0.05, $^{bb}P<0.01$, bubP<0.001, vs. IMN group.

Figure 14:
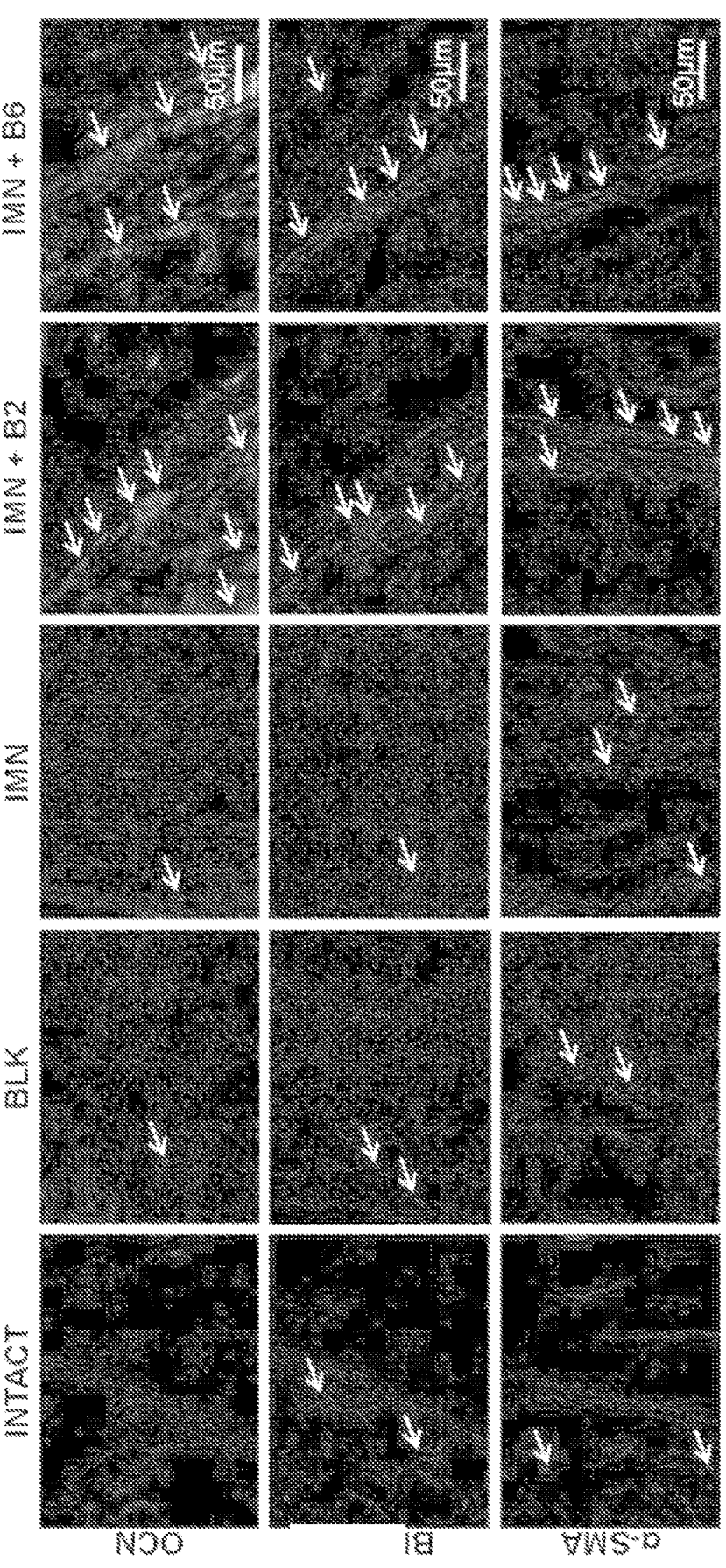

FIG. 14 shows according to an exemplary embodiment of the invention expression of osteocalcin (OCN), bone morphogenetic protein receptor II (BMPRII), or a-smooth muscle actin (a-SMA) in the periosteum of docking sites of the affected femurs on POD34. The animal groups included IM nail only group (IN), the 2 ug BMP-2-incorporated IM nail group (IMN+B2) and 6 g BMP-2-incorporated IM nail group (IN+B6). White arrows point to the positive expression of osteogenic marker OCN, BMPRII, or periosteum stem cell marker a-SMA stained by immunofluorescence.

Figures 15A, 15B, 15C, 15D, 15E, 15F:
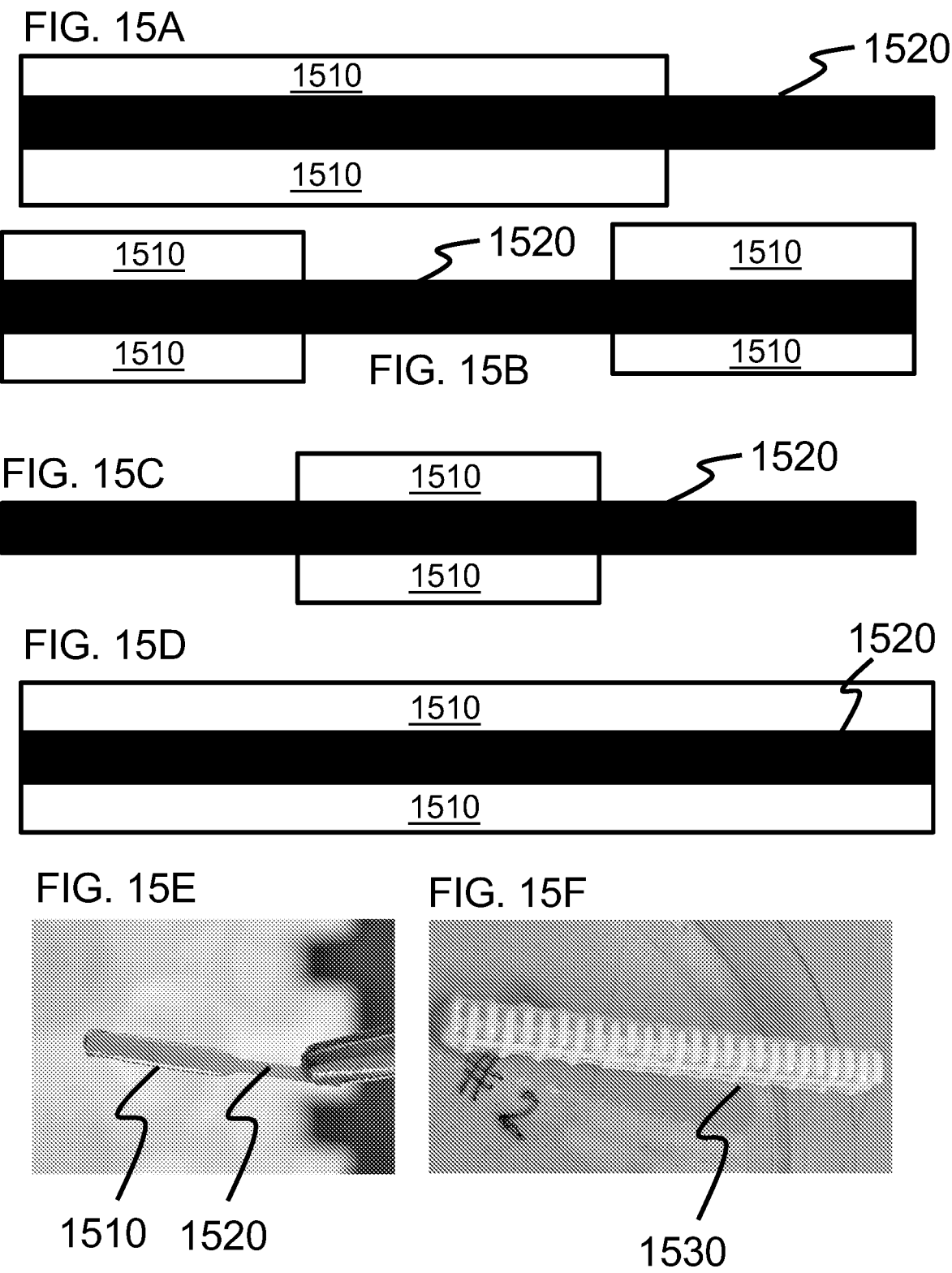

FIGS. 15A-F show according to exemplary embodiments of the invention the coating treatment applied to the entire structure or selected partial areas or structure of the rod or implant as needed. FIGS. 15A-D are schematics of the coating 1510 presence in the rod or implant 1520. FIGS. 15E-F are the schematics of the partially or entirely coated rod-shaped implant or 3D printed porous implant. FIG. 15A shows coating 1510 on one end, and 15B shows no coating in the middle portion of implant. FIG. 15C shows coating 1510 only in the middle portion of the implant. FIG. 15D shows coating 1510 on the entire implant. FIG. 15E shows coating 1510 on one end of the rod-shaped 1520 like implant. FIG. 15F shows coating 1510 covering and infiltrating the entire porous structure of the 3D printed implant 1530.

FIG. 16 shows according to an exemplary embodiment of the invention x ray images of bone regeneration in the defect treated with an Infuse Bone graft and a HyTEC implant in a sheep metatarsal bone transport model over time. POD indicates post operation day. For example, POD37 indicates 37 post operation days.

DETAILED DESCRIPTION

Definitions

The following detailed description is exemplary embodiments of the method of forming/making the tissue engineering construct and the structural features of the tissue engineering construct. In general, the following definitions of terms can be used as a guidance within the scope of the invention.

A scaffold is defined as a porous or non-porous three-dimensional construct made of polymers, ceramics, metals, or composites.

Treatment of a surface area includes the method of Base (e.g. NaOH) treatment, acid treatment, plasma treatment, freezing/thawing.

A treated surface to increase the surface area is defined as a surface with increased surface roughness due to a chemical or physical treatment (e.g. base, acid, plasma, or freezing/thawing).

Covalently linkable molecules to facilitate a chemical cross-linking to the surface area are Molecules that have a functional group for attachment to the surface and another functional group that can be bound to other molecules. Examples are Aminopropyl methacrylamide (APMA), Gelatin methacrylate (GelMA), and N-hydroxy succinimide) ester diazrine.

Salts are defined as a chemical that contains positively charged and negatively charged ions. Examples include calcium chloride and calcium sulfate. To stimulate surface-initiated physical crosslinking, calcium chloride ($CaCl2$)) or calcium sulfate ($CaSO4$) was deposited on the surface of the implants. Other salts of divalent cations (e.g. $Ca2+$, $Mg2+$, $Sr2+$, $Zn 2+$(zinc2+)) or multivalent cations (e.g. $Ti4+$ or $Al3+$) could also be used for surface initiated physical cross-linking.

Hydrogel precursor solution is defined as a solution that contains a crosslinkable polymer and an initiator.

Charged polymers are defined as polymers that carry negative charge or positive charge including alginate, polyglutamic acid, etc.

Covalently reactive macromonomers are defined as polymer molecules that carry chemically reactive groups.

Initiators are defined as chemicals that initiate a chemical reaction. Examples include photoinitators (e.g. Lithium phenyl-2,4,6-trimethylbenzoylphosphinate) and chemical initiators (e.g. Ammonium persulfate).

Biologics are defined as any molecules or organisms that can interact in living systems. Examples are proteins, peptides, cells, DNA, RNA, drugs, antibiotics.

Coating with one or more layers is defined as a single layer of coating with thickness in the 10-1000 µm range or multiple layers of coating each having thickness in the 10-1000 µm range.

Tissue Engineering is defined as engineering or regeneration of rigid or soft tissues including bone, cartilage, tendon, ligament, muscle, heart, heart valves, etc.

The following exemplary description addresses the question whether one would be able to accelerate bone healing and reduce nonunion in bone transport by introducing a biodegradable IM nail to sustain delivery of BMP in a single surgery procedure, without secondary operations, grafting, or severe complications. The objective(s) of the translational research and invention was to solve the clinical challenges such as prolonged, insufficient consolidation and high nonunion rate in large bone defect healing through a single treatment combining a clinically available surgical approach, distraction osteogenesis, with a novel bioengineering solution, an osteoinductive biodegradable IM implant device. To this end, the inventors first established a clinically relevant, rat bone transport model by developing a custom external fixator. Second, the inventors developed a novel BMP-2 eluting biodegradable IM implant device made of Food and Drug Administration (FDA)-approved materials and growth factors and examined their efficiency in sustained-release ex vivo. Third, the inventors investigated the effect of the novel BMP-2 eluting IM nails on bone consolidation and docking site union in the established rat bone transport model.

Results

Synthesis and Characterization of Intramedullary Nail Implant

Figure 1A:
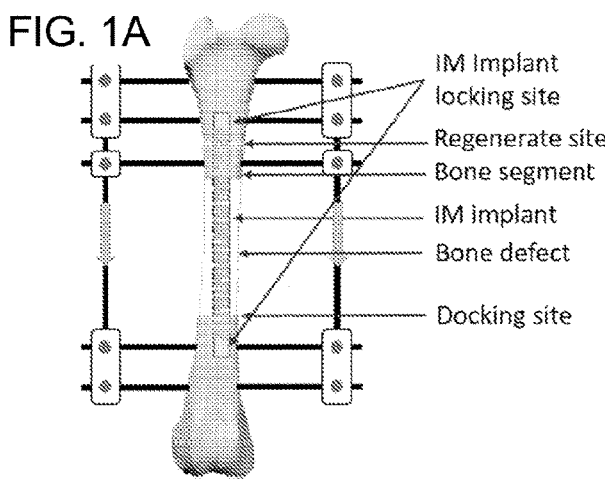
FIGS. 1A-D show according to an exemplary embodiment of the invention a schematic representation of the bioactive implant device for bone healing under three conditions. 'Blue color' represents the hydrogel coating. 'White dots' in the implant device represent porous structure.
Figure 1B:
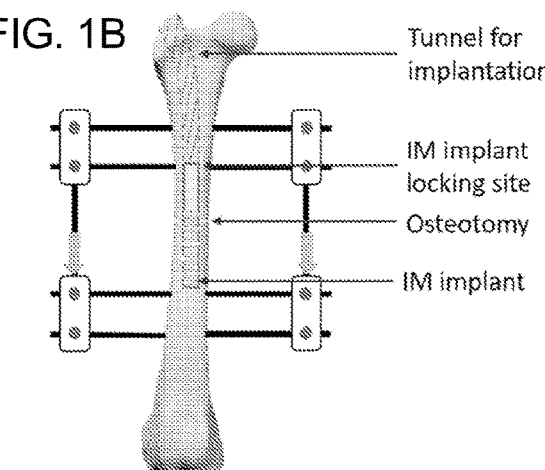
Figure 1C:
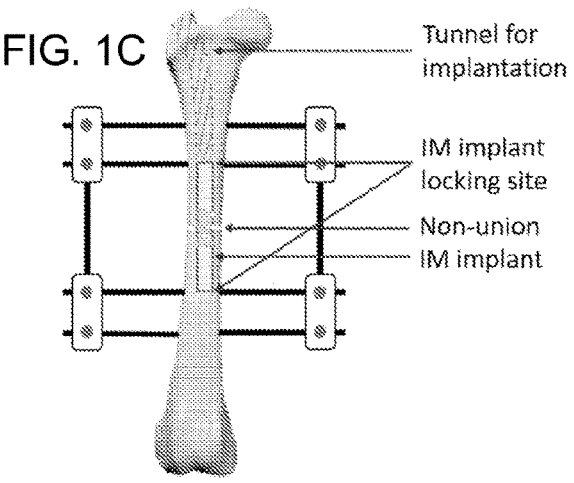
Figure 1D:
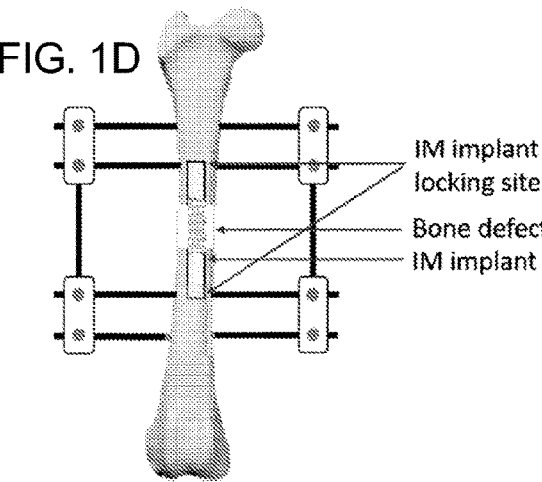
Figure 2A:
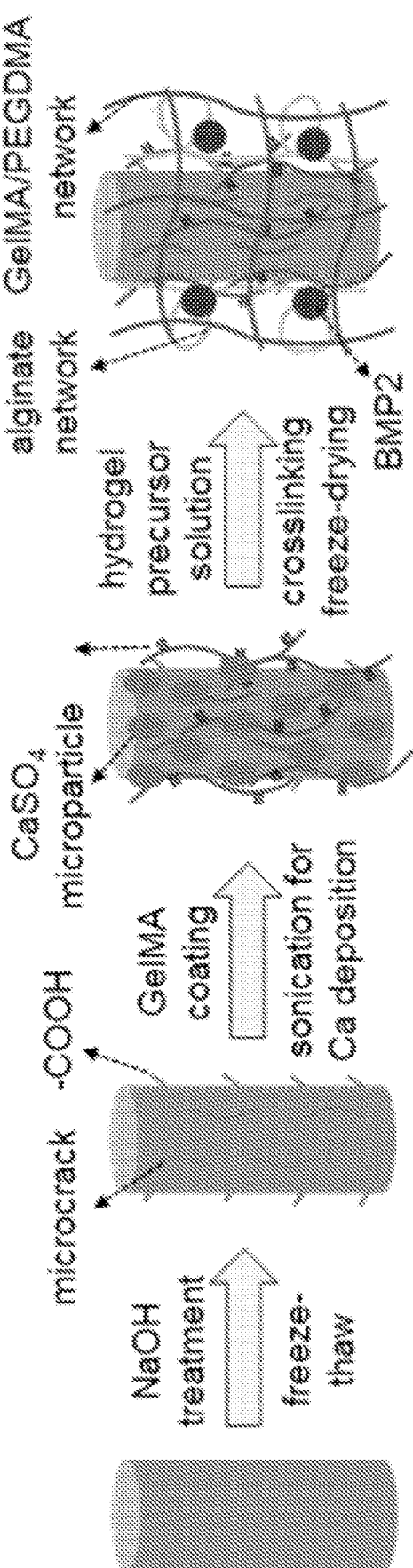
Figures 2B, 2C, 2D, 2E, 2F, 2G, 2H, 2I:
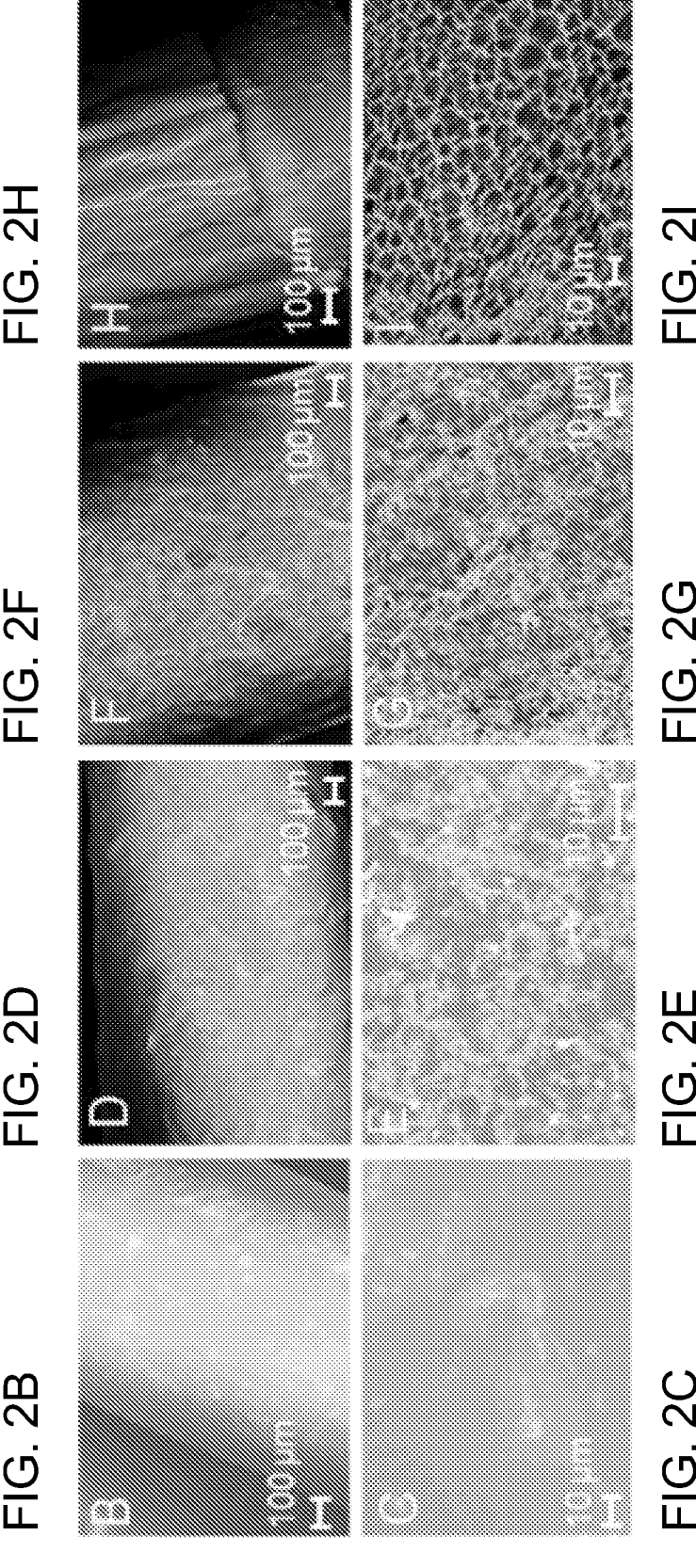
(FIGS. 2B-I) SEM images of the surface of PCL-TCP filaments after extrusion (FIGS. 2B-C), NaOH treatment and freezing/thawing (FIGS. 2D-E), GelMA coating and sonication in CaSO4 suspension (FIGS. 2F-G), and hydrogel coating (FIGS. 2H-I).

The procedure for making an osteoinductive biodegradable intramedullary nail implant is schematically shown in FIG. 2A. Following extrusion of polycaprolactone-beta-tricalcium phosphate (PCL-TCP, 80:20 in wt/wt) filaments (18.0 mm in length, 1.1 mm in diameter for each), the BMP-2-laden hydrogel was loaded onto the surface of the filaments in three consecutive steps as shown by the FIG. 2A. The scanning electron microscope (SEM) images of the surface of the PCL-TCP filaments corresponding to each step is shown in FIGS. 2B-I. As shown by the results, the surface of the filaments after NaOH treatment and freezing/thawing (FIGS. 2D-E) had higher roughness and microporosity compared with the surface of the filaments right after extrusion (FIGS. 2B-C). $CaSO_4$ microparticles were deposited on the surface of the filaments after GelMA coating and sonication in CaSO4 suspension (FIGS. 1F-G). A porous BMP-2-laden hydrogel layer with 8 μm average pore size was formed on the surface of the PCL-TCP filaments by surface-initiated physical crosslinking of alginate followed by covalent crosslinking of GelMA and PEGDMA (FIGS. 2H-I). The effect of chemical treatment (NaOH treatment and GelMA coating) without freezing/thawing or sonication (chem), chemical treatment with freezing/thawing but without sonication (chem+FT), and chemical treatment with freezing/thawing and sonication (chem+FT+sonic) on the tensile modulus of the PCL-TCP filaments is shown in FIG. 2J. There was not a significant difference between the tensile modulus of any of the treated filament groups (chem, chem+FT, or chem+FT+sonic) and the untreated rod group (no treatment). The effect of hydrogel loading and incorporation of BMP-2 on the weight of the implant is shown in FIG. 2K. The average weight of the filaments increased from 15.9 mg to 32.3 mg with hydrogel loading. The average percent loading of the hydrogel on the filaments was 112.5% and did not significantly change with adding 2 μg or 6 μg BMP-2 to the hydrogel (FIG. 2L). Representative images of a wet and freeze-dried BMP-2-laden hydrogel-loaded implant are shown in FIGS. 2M-N, respectively. The hydrogel layer was intact after freeze-drying (FIG. 2N). The diameter of filaments coated with hydrogel layer after freeze-drying were increased from 0.9 mm to 1.2 mm in average. The release kinetics of 2 μg or 6 μg BMP-2 from freeze-dried hydrogel-loaded implant over 28 days is shown in FIG. 2O. BMP-2 was released from the implants in a sustained manner over 21 days. Total amount of released BMP-2 from the implants that were loaded with 2 μg BMP-2 or 6 μg BMP-2 was 1.6 μg (80%) or 4.3 μg (71.7%) after 21 days and did not significantly change following day 21. At each time point the amount of released protein from the implants that were loaded with 6 μg BMP-2 was significantly higher than that of implants that were loaded with 2 μg BMP-2. To evaluate the storability of freeze-dried BMP-2-laden implants, the release kinetics of BMP-2 from the freeze-dried implants after 2 months storage at 4° C. was measured and compared with the release kinetics of BMP-2 from freshly made freeze-dried implants (FIG. 2P). There was not a statistically significant difference between total amount of released BMP-2 from fresh and stored implants at any time point in 28 days.

Ex Vivo and In Vivo Implantation of IMN in Bone Transport

Figures 3A, 3B, 3C, 3D, 3E, 3F, 3G, 3H:
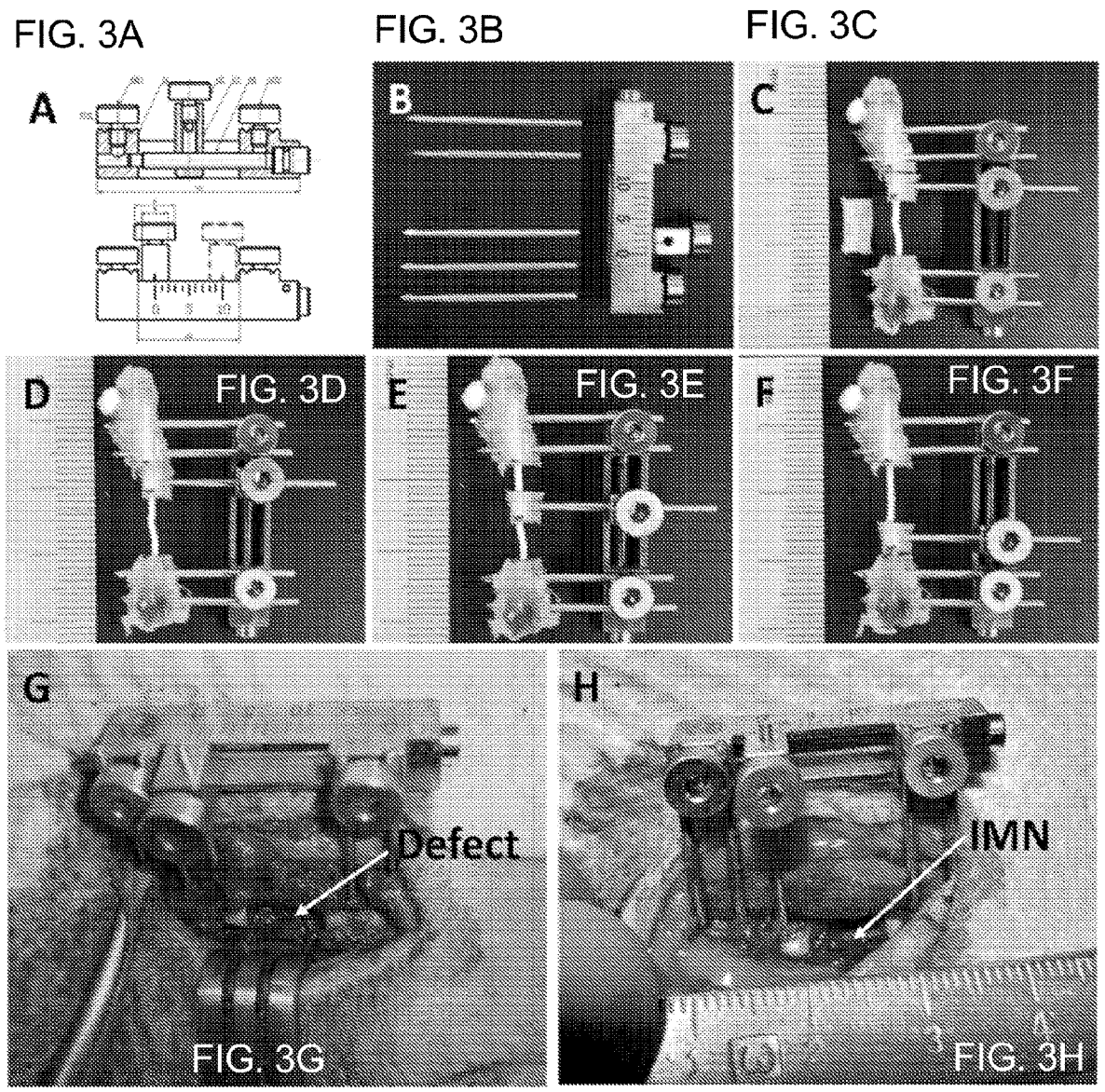
FIGS. 3A-H show according to an exemplary embodiment of the invention ex vivo and in vivo demonstration of bone transport by a customized metallic distraction fixator.

The movement performance of the distraction fixator was examined ex vivo in a femoral sample from an adult SD rat. First, the distraction frame was designed with two fixed ends and one movable part in between based on a basic bone lengthening fixator (FIG. 3A). The metallic distraction fixator consists of a monolateral frame and five fixative pins (FIG. 3B). The fixator was then used to fix the proximal and distal ends of a femoral sample and transport the bone slice over an IM Nail between the two ends in either an antegrade or a retrograde direction (FIGS. 3C-F). Five pins were drilled into the lateral site of the femur by a customized drill guide. An 8-mm osteotomy was made at the femoral shaft. Another 4-mm corticotomy for bone transport was also made. The 4-mm bone slice was then secured by a fixative pin drilled in the first cortical layer. An IM nail was put into the medullary canal, with its two ends fixed by the two close fixative pins, and also penetrating through the medullary canal of the 4-mm bone slice. Note that the middle pin was inserted without contact with the IM nail in the medullary canal. During the operations, the IM nails with or without BMP-2 coating were implanted into the animals (FIGS. 3G-H). After the operations, the animals were subjected to DO procedures. The DO procedures has three phases: a latency phase of 5 days, a lengthening phase of 8 days, and a consolidation phase of 21 (3 weeks) or 42 days (6 weeks).

From the gait performance as recorded on POD55 (after 6 weeks of consolidation), the inventors found the animal implanted with an IM nail without BMP-2 showed poor gait performance and, even a paralyzed gait after removing their fixators a week before (on POD48). Surprisingly, the animal moved fast and fluently when it was implanted with the IM nail coated with BMP-2 (2 g) and, with fixator removal on POD48, too. On POD34 or POD55, the femoral samples linking to the fixators were carefully harvested and preserved for further assessments (FIG. 4A).

The gross view of the samples after harvesting was observed. As shown by FIGS. 4A-B, most of the femoral samples showed nonunion at the docking site in the blank control (BLK) and IM nail only (IMN) groups, with the union rate increasing from 12.5% on POD34 to 25% on PODS5 in the BLK group, and from 0% on POD34 to 37.5% on POD55 in the IMN group. Pseudoarthrosis could be found at the docking sites in some of the specimens in the BLK and IMN groups (FIG. 4A). Surprisingly, all the femoral samples showed 100% union at the docking sites in the 2 ug BMP-2-incorporated IM nail group (IMIN+B2, POD34 or PODS5) and 6 μg BMP-2-incorporated IM nail group (IMN+B6, on POD34) (FIGS. 4A-B). However, the regenerate sites after bone transport in all the samples were found to have achieved 100% union. The union rate of the samples was double confirmed by micro-computed tomography (CT) analysis.

Figures 4A, 4B, 4C:
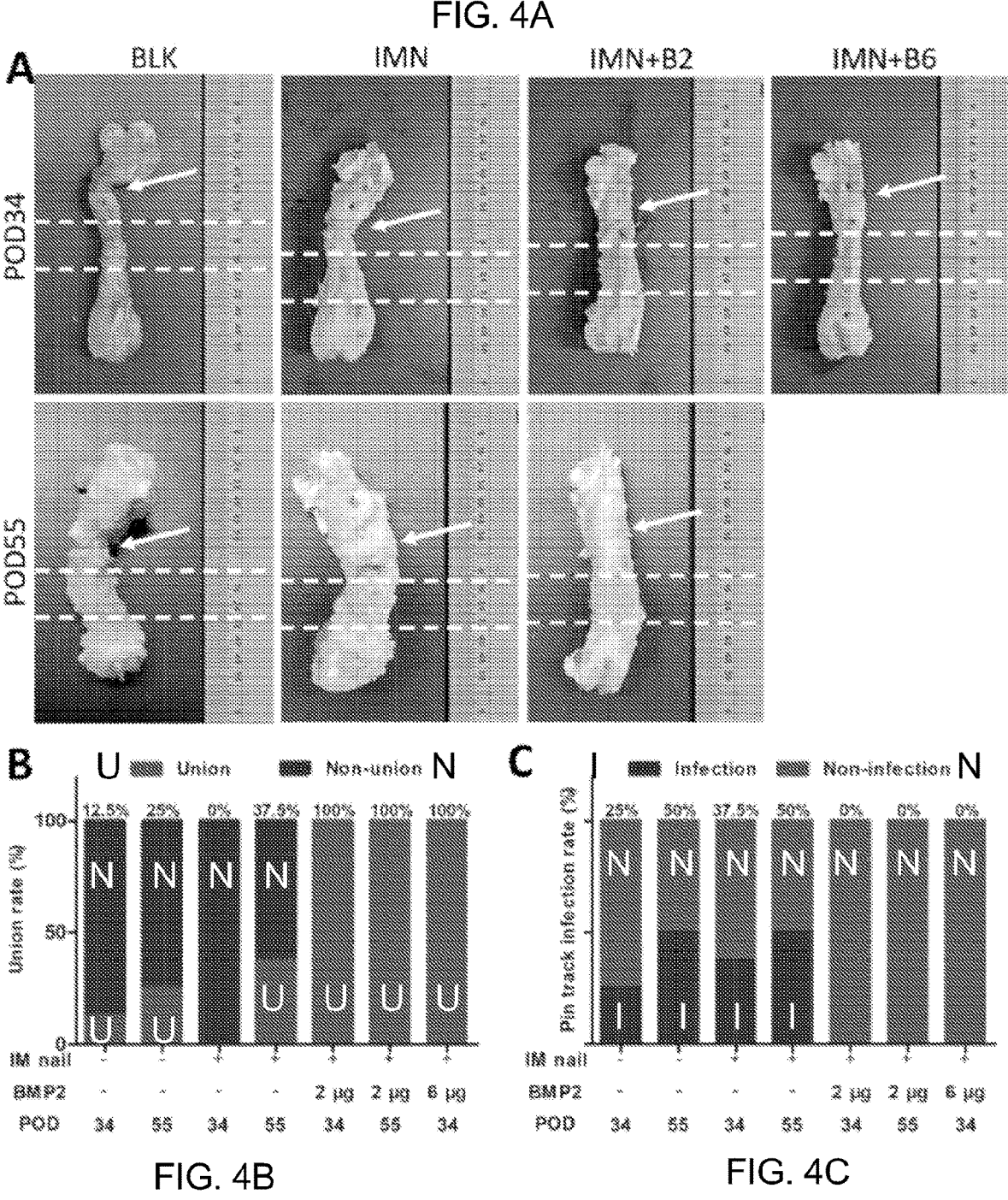
FIGS. 4A-C show according to an exemplary embodiment of the invention gross observation and union rate of the femoral samples harvested on POD34 or POD55. The animal groups included blank control group (BLK), IM nail only group (IMN), the 2 μg BMP-2-incorporated IM nail group (IMN+B2) and 6 μg BMP-2-incorporated IM nail group (IMN+B6).

After 3 or 6 weeks of consolidation, the animals showed minor infection at the pin sites but no major infections in the animals (FIG. 4C). However, the inventors did find minor pin track infections in many animals implanted without BMP-2 coating. The pin track infection was determined during the dis-assembling process of fixators before sacrifice. Although pin loosening was found in some animals, the external fixation can be continued during the study periods. Results showed that the pin track infection rate was 25% on POD34 or 50% on POD55 in the BLK group, and 37.5% on POD34 or 50% on POD55 in the IMN group (FIG. 4C).

Interestingly, when the animals were implanted with a BMP-2-incorporated IM nail, no infection occurred, regardless of the amount of BMP-2 incorporated or the timepoints of sacrifice (FIG. 4C).

2D and 3D Radiological Evaluation of Bone Healing

Dynamic X-ray imaging was performed to monitor the bone healing process. As shown by FIG. 12, an 8-mm bone defect could be found in each animal after the 5-day latency phase (PODS). After the 8-day lengthening phase, the 8-mm bone defect site could be found at the other site in each animal on POD13 (FIG. 12). After one week of consolidation (POD20), calluses could be found at the defect sites in the (IMIN+B2) group and (IMN+B6) group (FIG. 12). The mineral density of the calluses in the two BMP-2 incorporated groups were gradually increased through the consolidation phase (POD 20 to POD34) (FIG. 12). However, only a limited degree of callus formation was found in the blank control group or IM nail only group until POD34 (FIG. 12).

Figure 5A:
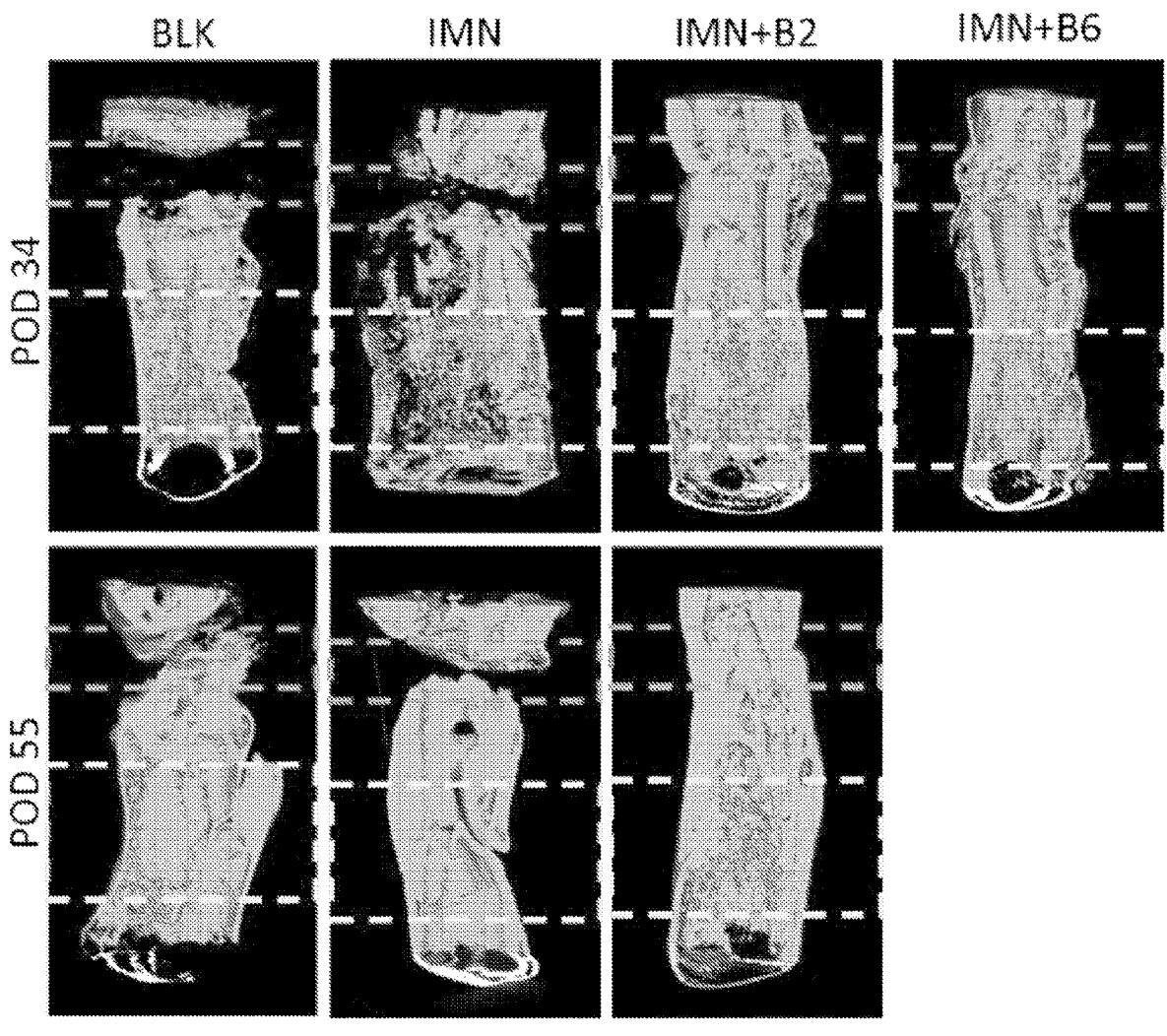
FIGS. 5A-C show according to an exemplary embodiment of the invention 3D reconstructed images and quantitative bone mass data of the affected femurs on POD34 or POD55 measured by micro-CT analysis. The animal groups included blank control group (BLK), IM nail only group (IMN), the 2 μg BMP-2-incorporated IM nail group (IMN+ B2) and 6 μg BMP-2-incorporated IM nail group (IMN+B6).
Figure 5B:
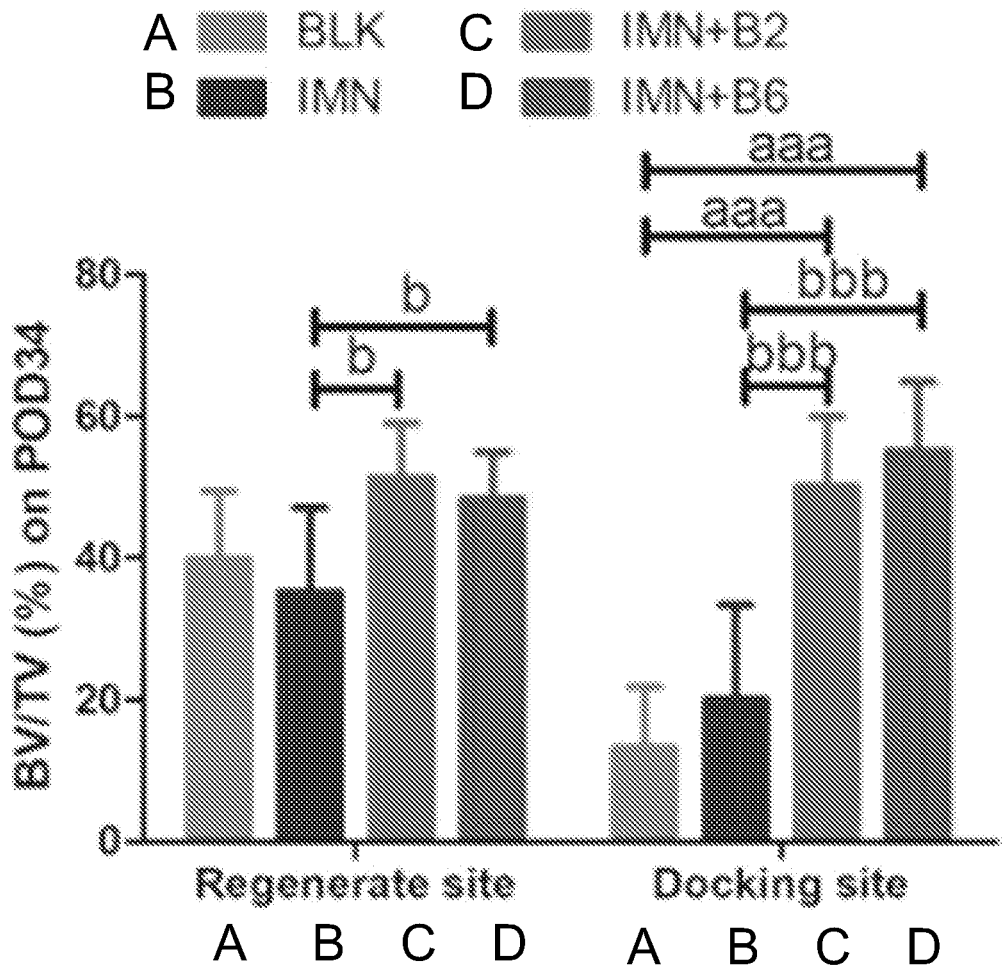
Figure 5C:
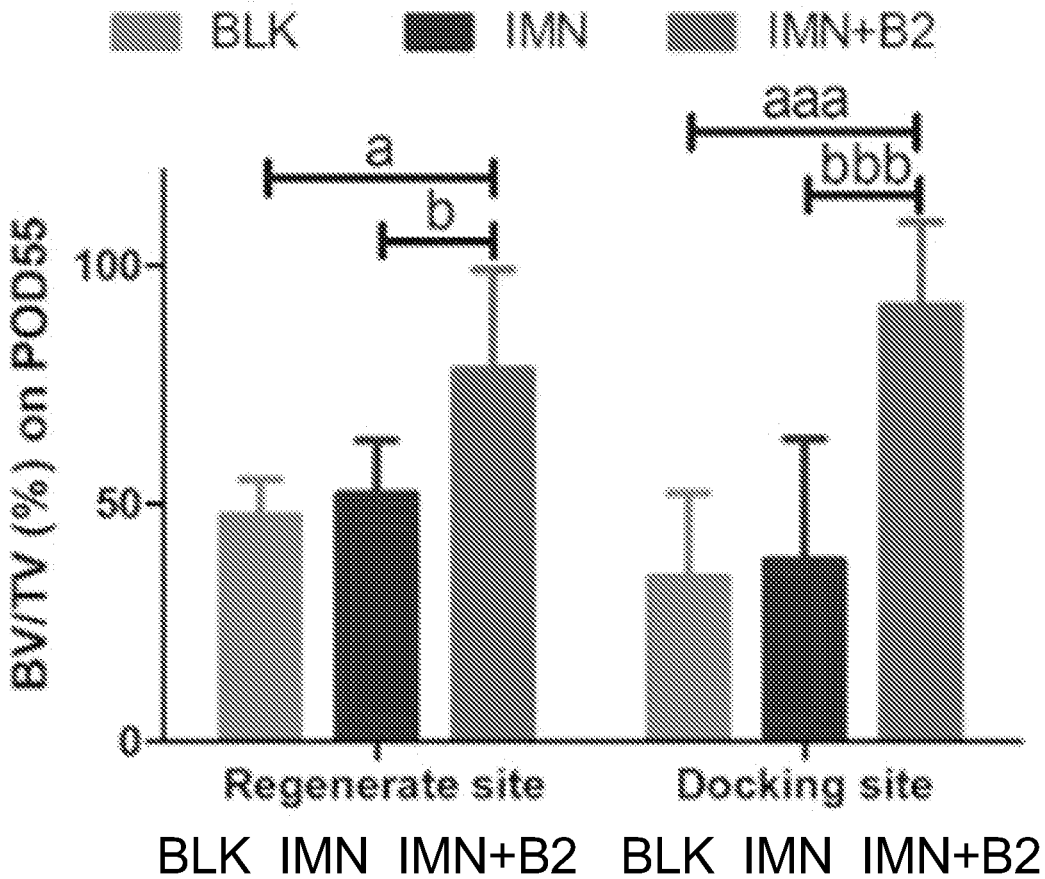

Micro-CT analysis was performed to reconstruct the 3D images of the affected femurs and to determine the quantitative bone mass in the two region of interests (ROIs), namely the bone defect site and the docking site on POD34 or POD55. As shown by the results, nonunion was found at the docking site in BLK group and IMN group on POD34 and POD55 (FIGS. 5A-C). In contrast, obvious bone fusion and remarkable increases in bone mass at the docking site were found in the (IMIN+B2) group (+30.1% in normalized BV/TV, P<0.001 on POD34; +53.4% in normalized BV/TV, P<0.05 on POD55) and (IMIN+B6) group (+35.2% in normalized BV/TV, P<0.001 on POD34) compared with those in the IMN group (FIGS. 5B-C). When compared with those in the BLK group, the normalized BV/TV was significantly increased by 36.8% (P<0.001) or 30.5% (P<0.001) in the (IMIN+B2) group, 41.9% (P<0.001) or 57.0% (P<0.001) in the (IMIN+B6) group, at docking site on POD34 or PODS5 (FIGS. 5B-C). However, newly formed bone could be found at the regenerate site in all the groups (FIG. 5A). Bone mass in the regenerate site was significantly increased in the (IMN+B2) group (+16.1% in normalized BV/TV, P<0.05 on POD34; +26.1% in normalized BV/TV, P<0.05 on POD55) and (IMIN+B6) group (+13.2% in normalized BV/TV, P<0.05 on POD34) compared with those in the IMN group (FIGS. 5B-C). At the regenerate site, there was no significant difference among the groups of BLK groups and BMP-2 incorporating groups on POD34 (FIG. 5B). However, there is no significant difference in the bone mass at the two ROIs between the two BMP-2 incorporated IM nail groups (FIG. 5B).

Mechanical Properties of the Affected Femurs

Three-point bending mechanical tests were performed to determine the mechanical properties of the femoral samples (FIG. 6A). The parameters, including maximum load, Young's modulus and energy absorption of the affected femurs were normalized by those of contralateral intact controls. Due to the high ratio of nonunion in BLK and IMN group, only a very limited number of femoral specimens were available to finish the entire mechanical test. For the nonunion samples, the mechanical parameters were set to zero as their failure in testing. As shown by the results, except for an increase in the energy resorption in the IMN group on PODS5, there is no significant difference in other mechanical parameters between the BLK group and IM nail group (FIGS. 6A-F). However, mechanical properties were remarkably enhanced in the (IMN+B2) group, increasing by 22.7% (P<0.01), 7.6% (P<0.05), or 18.6% (P<0.05) on POD34 (FIGS. 6A-C), or 34.1% (P<0.001), 30.4% (P<0.01), or 18.9% (P<0.001) on POD55 in normalized maximum load, Young's modulus, and energy absorption, respectively, compared with the BLK group (FIGS. 6D-F). In addition, when compared with those parameters in the IM group, mechanical properties were also found significantly enhanced in the (IMIN+B2) group, increasing by 22.2% (P<0.01), 7.3% (P<0.05), or 20.1% (P<0.05) on POD34 (FIGS. 6A-C), or 29.4% (P<0.001), 31.0% fold (P<0.01), or 7.5% (P>0.05) on PODS5 (FIGS. 6D-F) in normalized maximum load, Young's modulus, and energy absorption.

Mechanical properties were also significantly increased in the (IMN+B6) group by 26.6% (P<0.001), 11.6% (P<0.001), or 31% (P<0.001) in normalized maximum load, Young's modulus, and energy absorption when compared with those in the BLK group on POD34, or 26.1% (P<0.001), 11.3% (P<0.001), or 30.5% (P<0.001) when compared with those in the EVIN group on POD34 (FIGS. 6A-C). However, there is no significant different in the mechanical properties in the (IMN+B6) group when compared with those in the (IMN+B2) groups on POD43 (FIGS. 6A-C).

Histological Analysis

Figure 7:
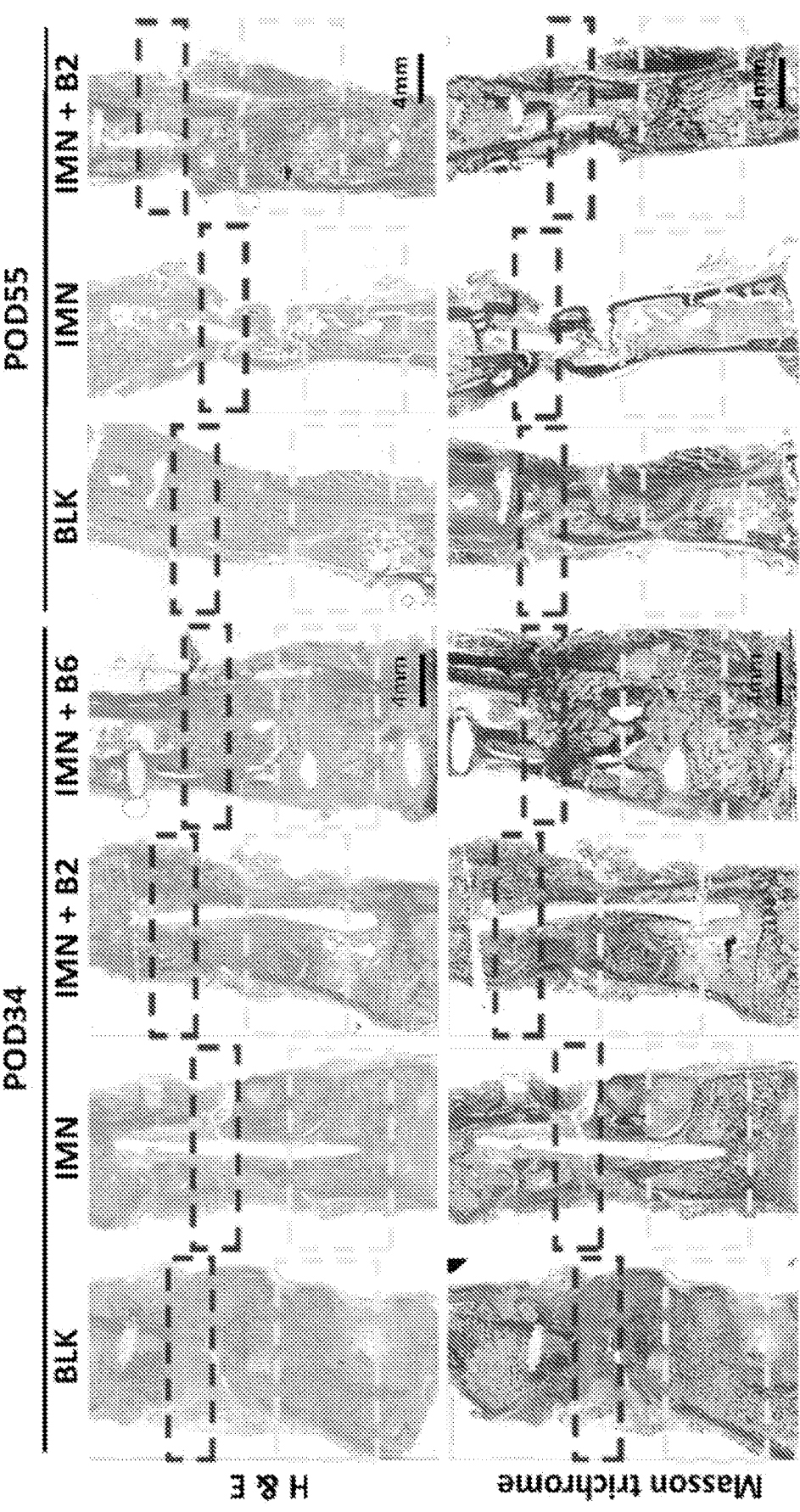
FIG. 7 shows according to an exemplary embodiment of the invention representative histological results of the affected femurs on POD34 or POD55. The animal groups included blank control group (BLK), IM nail only group (IMN), the 2 μg BMP-2 incorporated IM nail group (IMN+ B2) and 6 μg BMP-2-incorporated IM nail group (IMN+B6). Red dash rectangles indicate the docking sites. Yellow dash rectangles indicate the regeneration sites. Histology in this figure includes hematoxylin and eosin (H & E) staining and Masson Trichrome staining.
Figure 8:
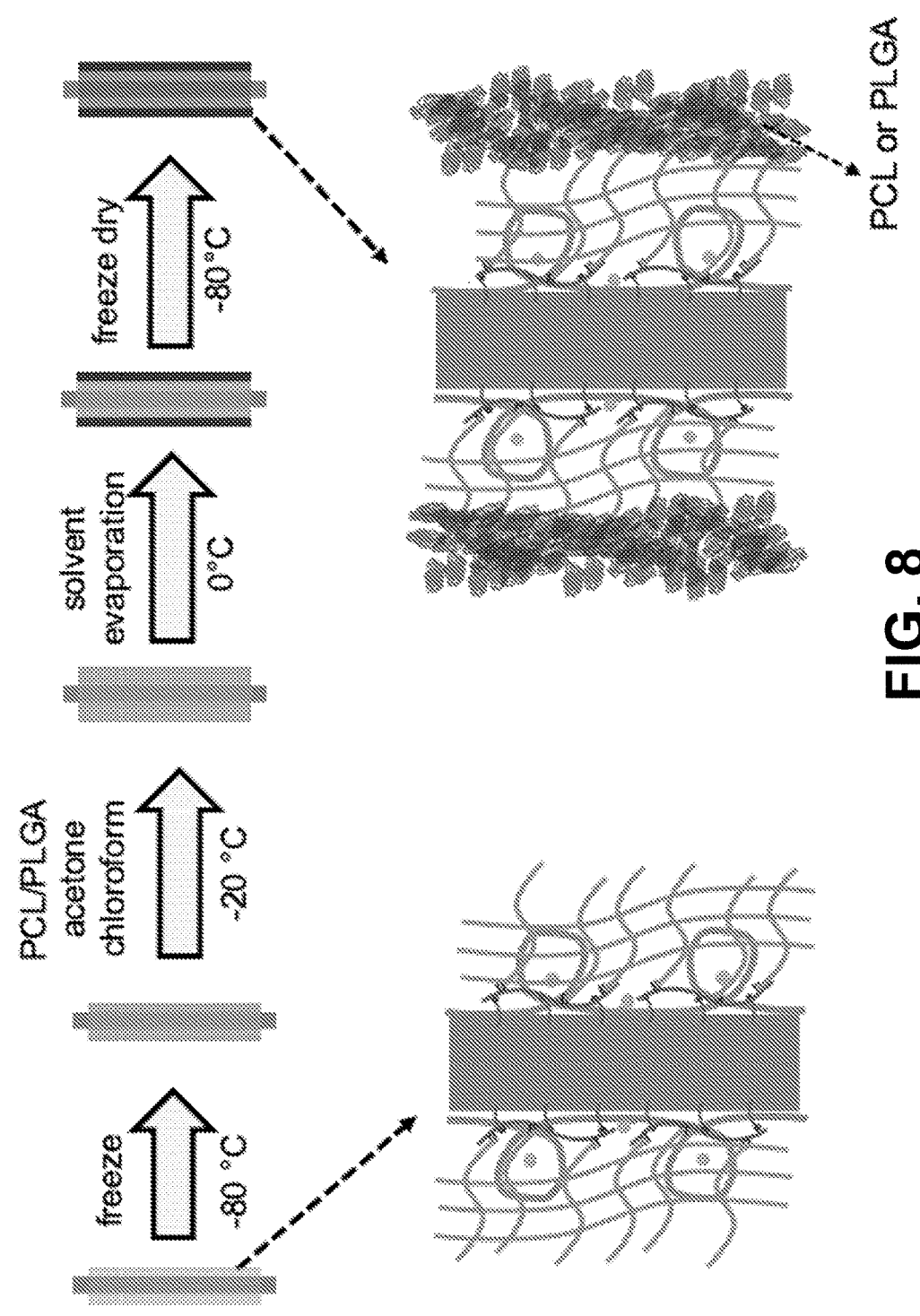
FIG. 8 shows according to an exemplary embodiment of the invention a schematic representation of the method that is used to coat the bioactive implants (HyTEC constructs).
Figure 9:
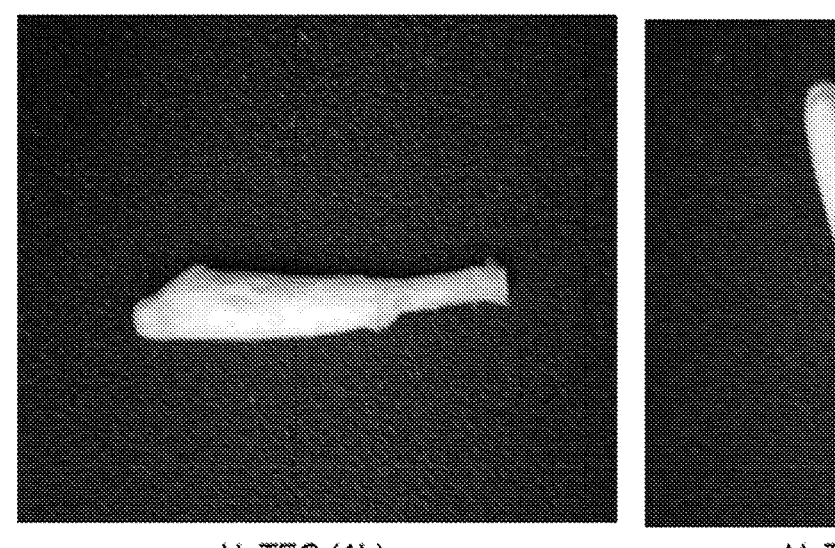
FIG. 9 shows according to an exemplary embodiment of the invention images of mHyTEC with 1 layer of PCL coating (mHyTEC (1 L)) and 3 layers of PCL coating (mHyTEC (3 L)) made using a PCL/acetone (10% wt/v) solution.
Figure 10:
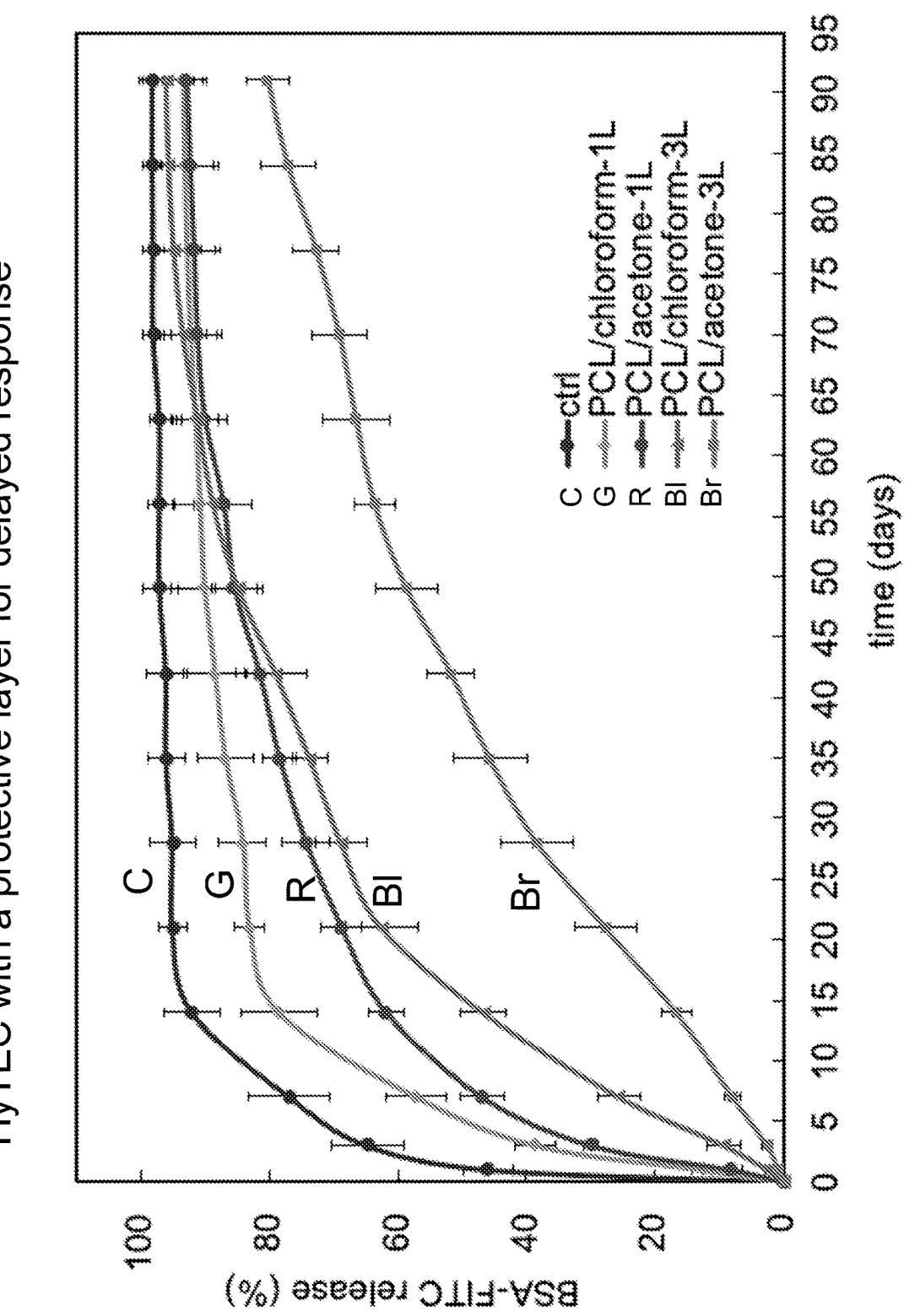
FIG. 10 shows according to an exemplary embodiment of the invention release kinetics of BSA from HyTEC constructs without PCL protective coating (ctrl), with 1 layer of PCL coating made using a PCL/chloroform (10% wt/v) solution (PCL/chloroform-1 L), with 1 layer of PCL coating made using a PCL/acetone (10% wt/v) solution (PCL/ acetone-1 L), with 3 layers of PCL coating made using a PCL/chloroform (10% wt/v) solution (PCL/chloroform-3

Histological data showed the longitudinal images of affected femurs, including the docking sites and regenerate sites (FIG. 7). From the results, the evidence was shown of soft tissue interposition at the docking sites of BLK group and the IMN group on POD34 and POD55 (FIG. 7). However, bony fusion was achieved at the docking sites in the (IMN+B2) and (IMN+B6) groups on POD34 and POD55, with no soft tissue interposition (FIG. 7). Newly formed bone could be found at regenerate site in all the groups on POD34 and PODSS (FIG. 7). Pin track infections could be found in some of the samples in the BLK and IMN groups on POD34 and POD35 (FIG. 7). Cortical and trabecular bone could be clearly identified at the regenerate sites as well as docking sites in the (IMIN+B2) group on POD55, indicating bone remodeling was also enhanced in the animals (FIG. 7). A much higher amount of newly formed bone could be also found at the implant site in the (IMN+B2) and (IMN+B6) group (FIG. 7).

Histomorphometry was performed to determine the dynamic mineral apposition at the docking sites as well as the regenerate sites of the affected femurs on POD34. From the images of in vivo fluorescent labels and the quantitative data, mineral apposition rate (MAR) was found to be significantly increased in (IMN+B2) and (IMN+B6) by 128.1% (P<0.001) and 126.0% (P<0.001) at the docking sites, and 21.0% (P>0.05) and 27.0% (P<0.05) at the regenerate sites, when compared with those in the BLK group (FIGS. 13A-B). Similarly, MAR was also significantly increased in (IMN+B2) and (MN+B6) by 142.6% (P<0.003) and 140.4% (P<0.001) at the docking sites, and 33.0% (P<0.05) and 39.6% (P<0.01) at the regenerate sites, when compared with those in the IMN group (FIGS. 13A-B).

To understand the underlying mechanism, immunofluorescence and immunohistochemistry staining have been performed. From FIG. 14, higher expression level was found of osteogenic marker (osteocalcin), BMP2 receptor II (BM-PRI), as well as the periosteum stem cell marker (a-SMA) in the (EIMN+B2) or (IMIN+B) group. These data indicate that bone formation was active at the docking sites, and periosteum stem cells involved in the healing process of docking sites. Highly expression level of BMPRII may facilitate BMP-2 binding to the osteogenic progenitor cells.

Considerations

A Long Bone Transport DO Model

The inventors successfully established a novel long bone transport DO model in rat which mimics the clinical environment and outcomes of human patients subjected to bone transport surgery, which typically exhibits normal bone regeneration at the regenerate site, but high morbidity rates of docking site nonunion and pin track infection. Previous studies have reported long bone transport models in relatively larger animals, such as sheep or rabbit. Canine or rabbit bone transport models were also found in the field of mandibular tissue reconstruction. To the best of the inventors' knowledge, this is the first report of a rat bone transport model. Rodent models are classically the first choice for in vivo testing in orthopedic research, due to the advantages of their accessibility and cost effectiveness before subsequent experiments in larger animal models and clinical studies. However, because of their smaller body size, rodents were rare used in previous bone transport experiments which require specialist surgical expertise and specialized hardware that allow for surgery and lengthening over time in a limited space. The inventors have custom designed and manufactured their own novel external fixator and drill guide for surgeries on long bone of rats, which facilitated the experiments in the study for this invention.

IM Nail as a Carrier for BiMP-2 Delivery

Wasserstein I is considered one of the pioneers in applying IM implant and the combination of an IM implant with external fixator. He operated in this way since 1963. However, a secondary tubular bone allografting was needed immediately after distraction. Paley first presented the concept of combining external fixator with an IM nail in situ in 1997 for shortening the period of wearing external fixator, IM nails are usually made of stainless steels or titanium alloys. The advantages of these metallic IM nail are higher patients' satisfaction, which is partially due to less social phycology concerns. The drawbacks are additional expense in IM nail and the removal of IM nail after consolidation may be needed.

As early as 1992, a biodegradable IM nail made from polyglycolic and polylactic acid co-polymers had been developed for intramedullary fixation. Results showed no significant difference in bone healing between the biodegradable IM nail group and the control group using Kirschner wires for the fixation of extraarticular fracture. Later, different types of antibiotic eluding IM nail apparatuses were developed for the fixation of fracture or other bone reconstruction procedures, as open wounds are exposed to bacterial or other infectious micro-organisms. A recent clinical study showed that a metallic IM nail with a core of polymethyl methacrylate cement with antibiotics presented lesser infection, faster consolidation, and fewer complications compared with standard nails in treating open fractures of tibia. However, the inventors found no such report in either patient or animal models in which bone transport was treated with a biodegradable IM nail. In this invention, osteoinductive biodegradable IM nail implants were manufactured using a novel technique for loading PCL-TCP filaments with a layer of BMP-2-laden hydrogel. PCL-TCP composites are biocompatible, mechanically stable, bioresorbable and osteo-conductive. However, PCL-TCP constructs lack osteo-inductive factors to stimulate osteogenesis and accelerate bone healing.

Surface coating has been used to immobilize proteins on the surface of scaffolds for tissue engineering applications. However, the amount of protein that can be loaded on the surface using surface coating is typically low and the release rate is fast. For instance, the amount of bovine serum albumin loading on hydroxyapatite-based scaffolds coated with chitosan and sodium hyaluronate by layer-by-layer (LBL) deposition, was lower and the release was faster than uncoated scaffolds. Hydrogels with their large water content and their porous microstructure provide a platform for adequate loading and sustained release of proteins. However, loading soft hydrogels on the surface of rigid constructs is challenging due to mechanical property mismatch at the interface. Furthermore, scaffolds loaded with protein-laden hydrogels via conventional techniques need to be used immediately after hydrogel loading to avoid water evaporation from the hydrogel and protein denaturation. IM nail implants in this work had a layer of BMP-2-laden hydrogel that was heavier than the PCL-ICP filament itself and integrated fully with the rigid filament surface. PCL-TCP filaments with a weight ratio of 80:20 maintained a rigid filament shape as the core of the IM nail which also kept remained stable when interlocked with the fixative pins in both ex vivo and in vivo studies. Following manufacturing PCL-TCP filaments via extrusion, the filaments were treated in consecutive steps to increase hydrophilicity, improve hydrogel adhesion, and stimulate surface-initiated crosslinking. NaOH treatment and freezing/thawing imparts hydrophilicity to the surface of polyesters due to the scission of ester bonds to carboxyl and hydroxyl groups and micropores formation on the surface, respectively. Coating of the surface with GelMA presented double bonds on the surface for covalent linking to the hydrogel. CaSO microparticles were deposited and entrapped on the soft surface of the GelMA modified filaments using sonication in $CaSO_4$ suspension at a temperature ($60°$ C.) close to PCL melting temperature (S). The results showed that any of the treatment steps did not adversely affect the tensile stiffness of the filaments. When the $CASO_4$ treated scaffolds were dipped into hydrogel precursor solution, the calcium ions diffused from the surface to the solution, crosslinked alginate at the proximity of the surface, and made a hydrogel layer on the surface. The GelMA and PEGDMA macromonomers within the physically crosslinked hydrogel were covalently crosslinked in the next step to form a stiff interpenetrating network. Also, HeMA was incorporated into the hydrogel for prolonging the release of BMP-2, due to a high affinity of heparin to BMP-2. It was shown that addition of HeMA to an alginate-based hydrogel extended the release kinetics of BMP-2 and improved subcutaneous bone formation in mice. The hydrogel that was loaded on the PCL-TCP filaments was heavier that the rod itself. Therefore, the method presented here could be used for loading an adequate dose of BMP-2 to stimulate in-vivo bone regeneration. Furthermore, the hydrogel network remained integrated with the PCL-TCP rod even after freeze-drying. According to the release data from freeze-dried BMP-2-laden implants with 2 lg or 6 Mg loaded BMP-2, 80.0% and 71.7% of the initial loaded BMP-2 was released after 21 days. The storage of BMP-2-laden implants for two months did not affect the activity and release kinetics of the BMP-2. Therefore, the method presented here could be used to manufacture storable osteoinductive biodegradable intramedullary nail implants.

From a clinical point of view, we have successfully fabricated a biodegradable IM nail by using the materials cleared by the Food and Drug Administration (FDA) for clinical applications, including PCL, TCP, alginate, as well as the bioactive factor th-BMP-2, and gelatin for food processing, a combination of which may form a promising medical device without many obstacles in future clinical applications. Among of these materials, PCL-TCP composites have attracted extensive attention in bone tissue engineering due to their high biocompatibility, long-term degradation, appropriate mechanical performances, and osteoconductivity. In this invention, PCL-TCP composites with a weight ratio of 80:20 maintain a rigid filament shape as the core of the IM nail, which also remained stable when they were interlocked with the fixative pins in both ex vivo and in vivo studies. GelMA/alginate composite hydrogel have been also frequently applied in drug or cell delivery, as the hydrogel possesses tunable mechanical property and excellent biocompatibility. As shown by the results, with an excellent integration to the PCL-TCP core, the GelMA/ alginate shell formed after freeze-drying possessed the ability of sustained-release of rhBMP-2 over 28 days with the aid of heparin, which protects BMP-2 from degradation and helps maintain its sustained-release property. In addition, the biodegradable IM nail exhibits excellent biocompatibility in the animals, with nearly the same ratios in pir track infection and docking site union as the blank control group, indicating a safe approach of this IM nail implantation. More and more studies have revealed that periosteum stem cells play a predominant role in DO-aiding bone defect healing. Although IM nail may have compromised the bone marrow by means of occupying the medullary canal after implantation, bone healing is preserved when the periosteum remains intact over the bone segments in this study. Evidence from clinical studies has already shown that metallic IM nails exert mechanical support without retarding bone healing during bone transport procedures.

BMP-2 and BMP-7 have been approved for clinical use in open fractures of long bones, nonunions and spinal fusion. However, BMPs should be delivered appropriately to achieve a satisfactory clinical outcome and avoid potential side effects. The main role of a delivery system for BMPs is to retain the growth factors at the site of bone injury for a prolonged time frame, providing an optimal biodegradability and mechanical support for tissue ingrowth. A prospective, randomized, controlled, and single blind clinical trial including 450 patients found that a BMP-2 implant (BMP-2 applied to an absorbable collagen carrier) was superior to the standard of care (intramedullary nail fixation and routine soft tissue management) in reducing secondary interventions, accelerating fracture and wound healing and reducing the infection rate in patients with an open fracture of the tibia. BMP-2 (25-750 µg per rabbit) or BMP7 (20 µg per rat) has also been locally applied by injection or spongy carrier to promote bone consolidation in bone lengthening in the rabbit or rat models, with a dose-dependent effect as shown by the densitometric results.

The current invention further demonstrated that even incorporated with a very low dose (2 µg per rat) of BMP-2, the IM nail was potent in promoting bone healing and accelerating fixator removal as early as POD48 (5 weeks of consolidation). This is the first report of a specific delivery of BMP-2 by means of intramedullary delivery through the biodegradable IM nail, which is compatible with the current practice, minimizes the interruption to the DO procedures while immobilizing its effect to promote local bone healing.

Bone Consolidation at Docking Site and Regenerate Site

The docking site nonunion has been recognized as a frequent problem in bone transport, resulting in substantial prolongation of the healing process, secondary operation of bone grafting, and delay of fixator removal. The docking site nonunion is believed to be caused by the inactive bone contact and substantial soft tissue interposition. As a cavity exists before the transported segment meets the target segment upon completion of the bone transport, the hematoma is gradually replaced with fibrocartilaginous tissue. The leading ends of the transported segment and the docking end of target segment are also sealed over by the fibrocartilaginous tissue %. The results from gross observation and imaging showed that the bone transport animal models treated with or without IM nail implants had a very low ratio of union (from 0 to 37.5%) at the docking site, even forming a pseudoarthrosis, which is consistent with the previous clinical outcomes. These results also indicated that IM nail itself had no effect on docking site consolidation. In the nonunion samples, we observed soft tissue interposition or even pseudoarthrosis at the docking site.

As described above, the docking site consolidation becomes the rate-limiting step inthe entire treatment process. Strategies to improve docking site consolidation have focused on surgical manipulation such as acute shortening, bone grafting, compression alternate compression-distraction, or bone marrow grafting combined with demineralized bone matrix. Exciting results from the current study showed that docking site union was achieved in all the animals treated with either 2 µg or 6 µg BMP-2 incorporated IM nails as early as POD34, with improvement in mechanical properties at both time points without any secondary operations or grafting. Results from immunofluorescence and immunohistochemistry revealed that the osteogenic marker (OCN), the periosteum stem cell marker periosteum stem cell marker (a-SMA), as well as BMPRII were highly expressed at the docking site periosteum. The inventors believed that BMP-2 releasing from the IM nail may have a positive effect on the docking site by means of maintaining active bone formation at the leading end and the docking end of the segments and facilitating bony fusion where the two ends meet. Such sustained BMP-2 eluting activated bone formation may also help prevent soft tissue invasion into the docking site or convert the migrating fibroblasts into bone tissue. The inventors hypothesized that migration and osteogenesis of periosteal stem cells residing at the two ends of docking site could be significantly enhanced by the BMP-2 released from the IMN implant, by binding to its receptor, BMPRII. However, further studies are needed to find out the exact underlying mechanism of sustained-released BMP-2 on the docking site.

Besides a satisfactory bone consolidation at the docking site, early consolidation at the regenerate site was also achieved in the BMP-2-incoporating groups, as shown by the higher BV/TV ratio analyzed by micro-CT and mechanical testing on POD55. Even though the mechanical testing data showed that the mechanical properties are not totally restored, the gait performance of the animals in the BMP-2-incoporating groups returned to normal after removing their fixators a week early (POD48), indicating enough maturation of the regenerate site to bear the weight of daily movements. The accelerated consolidation is due to the sustained release of BMP2 from the IM nail to the expanding vascular enriched soft regenerate at a consistent release rate controlled by the ratio of volume of lengthening to increased BMP2 exposure along the IM nail. The consolidation phase varies widely based on local and systemic health. However, the convention rate was reported at one week of consolidation for 1 mm of distraction in clinics. The rodent model results indicated that a higher consolidation rate at 1.6 mm per week of consolidation could be achieved via the BMP-2-incorporated IM nail even taking into consideration of species difference. It is very encouraging that in the BMP-2-incoporating groups, we also found the changes in BV/TV as measured by micro-CT and MAR as measured by histomorphometry in the regenerate site were not significant comparing with the BLK or IMN group at early time point (POD34), but only significant till the late stage of consolidation (PODS5). This is significant because these results suggest that our BMP-2 luting IM nail implants did not create an early premature consolidation to interfere with further lengthening in treating clinically relevant large bone defects in humans.

Clinical Indication and Prospective

The results presented and embodiments provided demonstrate a novel biodegradable BMP-2-incorporated IM nail implant safely and efficiently promoted consolidation at both regenerate site and docking site in the DO process, which facilitated early external fixator removal without any secondary operations. Given the promising results and most materials already cleared by FDA for medical applications, the inventors believe that the novel biodegradable BMP-2 incorporated IM nail has a great clinical translation potential in conjunction with bone transport technique.

IM nail implants could also be designed for in vivo studies in large animal or clinical trials in which a combination of hybrid 3D printing techniques with PCL-TCP porous scaffolds and GelMA-alginate-BMP-2 hydrogel coatings provide sufficient mechanical support, increasing the loading of BMP-2 and facilitating the vascularization after implantation. The inventors expect patients subjected to bone transport or limb lengthening to benefit largely by this single surgery approach, in which external fixators are removed at an earlier timepoint, secondary operations are avoided, and pin track infections are greatly reduced.

Materials and Methods

Study Design

The biodegradable implants were prepared as osteoinductive VIN grafts to guide the regeneration of 8-mm femoral segmental defects over bone transport DO. The implants comprise a composite of PCL/TCP (4/1) filament coated with freeze-dried hydrogel containing GelMA (15%), alginate (1.25%), PEGDMA (2%), HepMA (1%), and photoinitiator (0.3%) in deionized water loaded with BMP-2 (2 µg or 6 µg), The implants were characterized for their surface morphology, tensile strength, and protein release kinetics in vitro. The device was implanted in the medullary canal of a rat transport DO model. The DO protocol of this study consisted of 5-day latency, 8-day lengthening, and 21-day (POD34) or 42-day (POD55) consolidation. X-ray imaging, micro-CT analysis, mechanical testing, histology, and histomorphometry were performed to evaluate the efficiency of the IMN device in bone defect healing adjunctive to DO.

Chemicals

Medical-grade polycaprolactone (PCL, $M_n$=80 kDa) was purchased from Sigma-Aldrich. β-TCP nano-powder with average particle size of 100 nm (TCP) was purchased from Berkeley Advanced Materials Inc. N,N-Dimethylformamide (DMF), sodium hydroxide (NaOH), and ethanol were purchased from Fisher Scientific Inc. N-(3-Dimethylaminopropyl)-N'-ethylcarbodiimide hydrochloride (EDC), N-Hydroxysulfosuccinimide (NHS), 2-(N-Morpholino) ethanesulfonic acid (MES), N-(3-Aminopropyl) methacrylamide hydrochloride (APMA), gelatin type A, and heparin, and Calcium sulfate dihydrate (CaSO4) were purchased from Sigma-Aldrich. Polyethylene glycol dimethacrylate (PEGDMA, $M_n$=1000 gr/mol) was received from Polyscience, Inc. Sodium alginate (alginate, 500 GM) was purchased from Pfaltz & Bauer Inc. Human BMP-2 protein was provided by Medtronic. Human BMP-2 ELISA kit was purchased from Sigma-Aldrich.

Synthesis of PCL-TCP Filament

PCL-TCP filament with 0.9-mm diameter and PCL to TCP weight ratio of 80:20 was synthesized. Briefly, 80 g of PCL and 20 g of TCP were separately dissolved in 800 mL and 400 mL of DMF, respectively and stirred for 3 hrs at 80° C. The PCL and TCP solutions were then mixed, and the mixture was stirred for an hour. Then the mixture was precipitated in 4 liters of water to make PCL-TCP composite sheet. The PCL-TCP composite sheet was rinsed with water and residual solvent was evaporated inside of a fume hood at ambient temperature for 24 hrs. The dried PCL-TCP composite sheet was cut into pellets and extruded using an in-house built screw extruder.

Synthesis of Gelatin Methacrylate and Heparin Methacrylate

To synthesize GelMA macromonomer, gelatin was dissolved in deionized water (10% w/v) at 50° C. Methacrylic anhydride was added to gelatin solution at a molar ratio of 100:1 (methacrylic anhydride:gelatin) and the solution was allowed to react under stirring for 1 hr at 50° C. The mixture was then 5× diluted with deionized water and dialyzed against deionized water using a dialysis tube (Spectrum Laboratories, Rancho Dominquez, CA) with 6-8 kDa molecular weight cutoff for 3 days at 40° C. The GelMA solution was then freeze-driednd stored at –80° C.

To synthesize methacrylated heparin (HepMA), 1 g heparin was dissolved in 100 mL MES buffer (100 mM). 5 mL MES buffer containing 45 mg EDC and 30 mg NHS was then added to the heparin solution to activate the carboxylic acid groups. After 1 hr reaction at room temperature, 25 mg APMA in 1 mL MES was added to the solution and allowed to react for 2 hrs at room temperature. The HepMA solution was then dialyzed against deionized water using a dialysis tube (Spectrum Laboratories, Rancho Dominquez, CA) with 6-8 kDa molecular weight cutoff for 3 days at ambient temperature, lyophilized, and stored at –80° C.

Coating PCL-TCP Filaments with BMP-2-Laden Hydrogel

The procedure for coating PCL-TCP filaments with BMP-2-laden hydrogel is schematically shown in FIG. 2A. PCL-TCP filaments with 0.9 mm in diameter were synthesized, manually cut to make 18 mm filaments, and dipped into a 5N NaOH solution for 6 hrs. The filaments were then washed three times with deionized water and incubated in an MES buffer (100 mM) containing EDC (5 mg/mL) and NHS (5 mg/mL) for 30 mins at room temperature in order to activate the carboxylic acid groups on the surface. Then, the filaments were washed three times with deionized water and incubated in gelatin methacrylate (GelMA) 2% solution in MES buffer for 1 hr at 37° C. The filaments were then washed three times with deionized water to remove the unreacted GelMA and incubated in EDC/NHS (5 mg/mL) in MES buffer solution for 15 mins at room temperature. The GelMA coated filaments were then washed three times with deionized water and dried under vacuum. Then, the GelMA coated filaments were dipped into a CaSO4 suspension in deionized water (100 mg/mL) at 60° C. and sonicated for 30 secs. The filaments were then transferred into wells of a 24-well plate and dried under vacuum. The dried filaments were dipped into wells of a 96-well plate containing GelMA (15%), Alginate (1.25%), PEGDMA (2%), HepMA (1%), protein (BMP-2, 200 µg/mL), and photoinitiator (0.3%) in deionized water at 37° C. for 2 mins. The hydrogel-loaded filaments were removed from the solution and left in dry wells of another 96-well plate for 5 mins. The hydrogel-loaded filaments were then irradiated with visible light for 15 mins to covalently crosslink GelMA, PEGDMA, and HepMA. The crosslinked hydrogel-loaded filaments were stored at –80° C. and freeze-dried.

Tensile Modulus, Hydrogel Loading and Surface Morphology Characterization

Tensile modulus of PCL-TCP filaments was measured using an Instron 5944 uniaxial testing system with a 2 kN load-cell (Instron Corporation, Norwood, MA) and iN pre-load. Tensile modulus measurement was performed at a displacement rate of 1% strain/s up to 25% strain. The slope of the linear regime of the stress vs strain curve was taken as the tensile modulus. 5 samples per group were used for tensile modulus measurements.

The hydrogel loading (%) was calculated from the scaffold weight before hydrogel loading (Wb) and after hydrogel loading (Wa), using the following equation. 8 samples per group were used for hydrogel loading measurements.

$$\text{hydrogel loading} = 100 * (Wa - Wb)/Wb$$

For visualizing the surface morphology, the filaments were immersed in liquid nitrogen and freeze-dried. The hydrogel samples were then coated with gold using a SPI sputter (SPI Supplier Division of Structure Prob, Inc., West Chester, PA) for 180 seconds and imaged using a Field Emission Scanning Electron Microscope (Zeiss Sigma, White Plains, NY) at an accelerating voltage of 5 keV.

Protein Release

For measurement of release kinetics, hydrogel-coated filaments with 2 µg or 6 µg encapsulated BMP-2 were freeze-dried and incubated in 1 mL PBS at 37° C. for 28 days. At each time point, the amount of BMP-2 in the release medium was measured using ELISA and the release medium was replaced with fresh PBS. In order to investigate the effect of implant storage on the protein activity and release kinetics, BMP-2-laden hydrogel-coated filaments were stored for 2 months at 4° C. and then the release kinetics of BMP-2 from the stored implants was measured and compared with those of freshly made implants.

Design of External Distraction Fixator for Bone Transport

A monolateral external distraction fixator was specifically designed and customized for bone transport in a SD rat model. The fixator consists of two parts: one frame (32 mm in length) and five fixative pins (1.2 mm in diameter, 22 mm in length). The frame has two fixed ends, which were used to lock two pins at each end, and to fix proximal and distal bone segments after osteotomy. The frame also has one movable part between the two fixed ends, which was used to lock the last pin to fix a movable bone slice after corticotomy. The performance of the fixators was tested ex vivo in a femoral sample from a 12-week old SD rat.

Animal Surgery and DO Protocol

Before surgery, each rat was anaesthetized with 2-3% isoflurane (VetOne, Boise, ID) during operation on a heating pad. Cefazoline (25 mg/kg) was then injected subcutaneously to the animals. After disinfection, a 25-mm incision was made along the lateral site of left femur. Four pins were drilled through the bone for fixation. Another pin was drilled through the first cortical bone only for bone transport, and then the frame was placed to fix the bone. A femoral transverse osteotomy procedure at the midshaft was performed by a wire diamond saw to remove an 8-mm bone slice under sterile conditions. A 4-mm transverse corticotomy for bone transport was further carried out at distal femur. The prepared IM nail devices with a length of 18 mm and diameter of 1.2 mm were inserted into the medullary canal of proximal and distal femoral segments, with the two ends secured by the proximal and distal fixative pins. The IM nails were coated with 0 µg (IMN, n=16), 2 µg (IMN+B2, n=16) or 6 µg (IMN+B6, n=8) BMP-2-incorporated hydrogel as described above. The animals without IM nail implantation were regarded as blank controls (BLK, n=16). Surgical incisions were then sutured sequentially. The DO protocol of this study has three phases according: a latency phase of 5 days (from operation date to post operation day (POD) 5), a 8-day active lengthening phase (0.5 mm/12 hrs, from POD5 to POD13), and a consolidation phase of 21 (from POD13 to POD34) or 42 (from POD13 to POD55) days. Bone transport was performed over the IM nail in a retrograde direction in our animal study.

Post-Operation Care and Sample Harvest

Animals were housed individually after operation. Pin track infection was monitored and managed in all the animals during the study period. Polyvinylpyrrolidone iodine and ethanol were used during pin track care when required. Pin track infections were monitored and classified accordingly to the Checketts-Otterburn classification. According to this system, pin track infections are classified into two groups, minor (Grades 1-3) and major (Grades 4-6). Three rats in each group were randomly selected and received subcutaneous injection of xylenol orange (30 mg/kg, Sigma-Aldrich, St. Louis, MO, USA) at 13 days before termination (POD34) and calcein (10 mg/kg; Sigma-Aldrich, St. Louis, MO, USA) at 3 days before termination (POD) for in vivo labeling. The general gait performance of animals was observed on POD54 with fixator removal one week prior (POD48). All the animals were sacrificed and both femurs were harvested for qualitative and quantitative assessments on POD34 or POD55. Of note, for the (IMN+B6) group, all of the 8 rats were sacrificed on POD34. Bone union was primarily evaluated by gross observation of the specimens and further confirmed by micro-CT analysis as described below. Specimens were fixed in 10% buffered formalin for 48 hrs and then transferred to 70% ethanol for preservation.

Dynamic X-Ray Imaging

The dynamic changes in bone defect healing were monitored by LAGO-X in vivo imaging system (Spectral Instrument Imaging, Tucson, AZ) weekly from POD5 to POD34 in all the animals. At first, animals were anaesthetized by 3% isoflurane in an induction chamber. Then each animal was transferred to the heated imaging platform and positioned in upside down before imaging. The imaging parameters were set to 40 keV and 18 seconds in exposure.

Micro-Computed Tomography (CT) Analysis

Microstructural change within the distraction regenerate and docking sites in the animals was qualitatively and quantitatively assessed using micro-CT. Briefly, all the specimens were imaged using Skyscan 1276 micro-CT (Bruker, Kontich, Belgium) at a custom isotropic resolution of 20 um isometric voxel size with a voltage of 70 kV and a current of 200 A. with a rotation step of 0.8° and in 360° scan mode. Beam hardening reduction was applied using a 0.5 mm Al filter. The projection images were reconstructed off-line using a cone beam NRecon application (version 1.0.7.0., Bruker) with post-alignment and beam hardening corrections for image analysis. Post processing of the reconstructed images was analyzed using the SkyScan CAn software package (version, 1.17, Bruker). Two regions of interest (ROIs) were analyzed separately, including the lengthening zone (8-mm in length) and the docking site (1.5 mm in length). Cross-sectional slices of the lengthening zone or docking site were used for bone tissue volume fraction Bone volume/total volume, BV/TV) measurement by CTan. BW/TVs of the ROIs were normalized by those in contralateral intact control. 3D bone structure was made from the segmented dataset with CTAn (CT Hounsfield units (HU) threshold >10000) for visual inspection using the MicroView 3D Image Viewer (Version 2.5.0, Parallax Innovations Inc., Ilderton, Canada). Nonunion was confirmed by Micro-CT analysis, which was defined by no radiographic evidence of bone fusion at regenerate site or docking site.

Mechanical Test

After micro-CT analysis, mechanical properties of specimens were evaluated by three-point bending test within 24 hrs after termination. A material testing system Instron 5944 testing system, Norwood, MA) with a 2 kN load cell was used to test the femurs to failure. The femurs were loaded in the anterior-posterior direction with the inner and outer span of the blades set as 8 and 18 mm, respectively. The bones were tested at a speed of 0.01 mm/s, with the long axis of the femur placed perpendicular to the blades during the test. The modulus of elasticity in tension (Young's modulus), maximum load, and energy to failure were obtained and analyzed with built-in software (OMAT Professional; Tinius Olsen, Inc., Horsham, PA, USA). The biomechanical properties of the new bone were expressed as percentages of the contralateral intact bone properties. During the mechanical tests, the inventors ended the compression testing once the loading showed a 15% decrease to prevent breaking of the bone.

Histology

Immediately after mechanical tests, the specimens were initially fixed in 10% formalin for 48 hrs, then transferred to 70% ethanol. The specimens (n=5 per group) were decalcified in 10% EDTA solution for 5 weeks and embedded in paraffin after dehydration with ethanol. Thin sections (5 um) were cut by a microtome (RM2525, Leica, Germany) along the long axis of each femur in the sagittal plane. The slides were stained with hematoxylin and eosin (H&E; Sigma-Aldrich, St Louis, MA) or Masson Trichrome staining (Abcam, Cambridge, MA) following standard protocol.

Histomorphometry

For histomorphometry, a protocol for paraffin embedding of mineralized bone was applied in this study. After fixation, some of the specimens (n=3) were treated with 5.0% (w/v) aqueous potassium hydroxide for 96 hours at room temperature on an orbital shaker. Then the bones were washed with water and then dehydrated in ethanol under a vacuum infiltrating system. Processed bones are embedded routinely into paraffin blocks. 10-um sections were cut by a RM2255 microtome (Leica, Wetzlar, Germany) along the long axis of each femur in the sagittal plane. For histomorphometry, two sections with 100 um apart were selected for measurements. Fluorescent images were taken under an All-in-One Fluorescence Microscope BZ-X800 (Keyence, Osaka, Japan). 5 random images at 10× magnification at the docking site or regenerate site were applied for measurements. Mineral apposition rate (MAR) was determined by the distance between red and green labels, divided by the 10 days interval.

Immunofluorescence and Immunohistochemistry

Immunofluorescence and immunohistochemistry assays were performed using standard protocols. Samples were incubated with anti-osteocalcin (Santa Cruz, Dallas, TX), anti-BMPRII (Santa Cruz, Dallas, TX) or anti-a-SMA antibody (Santa Cruz, Dallas, TX) overnight at 4° C. For immunofluorescence, Alexa Fluor 488, 594 or 647-conjugated secondary antibodies (Abcam, Cambridge, MA) were used. For immunohistochemistry, a horseradish peroxidase-streptavidin detection system (Dako, Santa Clara, CA) was used, followed by counterstaining with hematoxylin.

Statistical Analysis

All the quantitative data were presented as mean and standard deviation (SD). After checking of normal distribution by the Kolmogorov-Smirnov test, all parameters were analyzed by ANOVA and post ho Turkey's HSD. For micro-CT analysis and mechanical testing, contralateral femurs were used to normalize the parameters. The statistical analysis was calculated by SPSS (version 16.0; SPSS Inc, Chicago, IL) and the level of significance was set at $P<0.05$.

Benefit

The present invention claims the benefit, or priority, to U.S. Provisional Applications 63/289,431 filed Dec. 14, 2021, 63/304,216 filed Jan. 28, 2022, 63/289,447 filed Dec. 14, 2021, and 63/304,207 filed Jan. 28, 2022 all of which are incorporated herein by reference for all that they teach.

What is claimed is:

1. A method of reconstructing a bone defect, deformity or nonunion, comprising:
   (a) providing a freeze-dried bioactive orthopedic implant, wherein the freeze-dried bioactive orthopedic implant comprises:
      (i) a scaffold comprising a treated surface area,
      (ii) a hydrophilic hydrogel network, comprising:
         a) a charged polymer physically cross-linked to the scaffold,
         b) covalently reactive macromonomers chemically cross-linked to the scaffold, and
      (iii) one or more biologic agents within the hydrophilic hydrogel network; and
   (b) implanting the freeze-dried bioactive orthopedic implant into a patient in need thereof, wherein the implant provides sustained-release of the one or more biologic agents.

2. The method of claim 1, wherein the scaffold is a rod.

3. The method of claim 1, wherein the scaffold is porous.

4. The method of claim 1, wherein the scaffold comprises polycaprolactone-beta-tricalcium phosphate (PCL-TCP).

5. The method of claim 1, wherein the surface of the scaffold is treated with an acid or a base.

6. The method of claim 1, wherein the surface of the scaffold is treated with a base.

7. The method of claim 1, wherein the hydrophilic hydrogel network comprises polymerized aminopropyl methacrylamide (APMA), gelatin methacrylate (GelMA), polyethylene glycol dimethacrylate (PEGDMA), or a combination thereof.

8. The method of claim 1, wherein the surface of the scaffold is treated with a salt.

9. The method of claim 8, wherein the salt comprises a calcium salt, magnesium salt, strontium salt, zinc salt, aluminum salt, titanium salt or a combination thereof.

10. The method of claim 8, wherein the salt comprises a calcium salt.

11. The method of claim 1, wherein the charged polymer comprises alginate.

12. The method of claim 1, wherein the charged polymer is physically crosslinked to the scaffold via an ionic interaction.

13. The method of claim 12, wherein the ionic interaction is between a calcium salt on the surface of the scaffold and the charged polymer.

14. The method of claim 13, wherein the calcium salt comprises $CaSO_4$, $CaCl_2$ or a combination thereof.

15. The method of claim 1, wherein the covalently reactive macromonomers comprise gelatin methacrylate (GelMA) and polyethylene glycol dimethacrylate (PEGDMA).

16. The method of claim 1, wherein the biologic agents comprise a growth factor.

17. The method of claim 16, wherein the growth factor comprises bone morphogenetic proteins (BMP).

* * * * *